United States Patent
Mei

(10) Patent No.: US 11,530,350 B2
(45) Date of Patent: Dec. 20, 2022

(54) LIGAND AND METHOD OF MANUFACTURING THE SAME, QUANTUM DOT FILM AND METHOD OF MANUFACTURING THE SAME, AND DISPLAY APPARATUS

(71) Applicant: BOE TECHNOLOGY GROUP CO., LTD., Beijing (CN)

(72) Inventor: Wenhai Mei, Beijing (CN)

(73) Assignee: BEIJING BOE TECHNOLOGY DEVELOPMENT CO., LTD., Beijing (CN)

( * ) Notice: Subject to any disclaimer, the term of this patent is extended or adjusted under 35 U.S.C. 154(b) by 0 days.

(21) Appl. No.: 17/032,546

(22) Filed: Sep. 25, 2020

(65) Prior Publication Data

US 2021/0095194 A1   Apr. 1, 2021

(30) Foreign Application Priority Data

Sep. 27, 2019   (CN) .......................... 201910927985.5

(51) Int. Cl.
| | |
|---|---|
| *C07C 323/25* | (2006.01) |
| *C09K 11/02* | (2006.01) |
| *H01L 51/00* | (2006.01) |
| *H01L 51/50* | (2006.01) |

(52) U.S. Cl.
CPC .......... *C09K 11/025* (2013.01); *C07C 323/25* (2013.01); *H01L 51/0077* (2013.01); *H01L 51/502* (2013.01)

(58) Field of Classification Search
CPC .......................... C07C 323/25; H01L 51/0077
USPC ......................................................... 568/22
See application file for complete search history.

(56) References Cited

U.S. PATENT DOCUMENTS

| | | | |
|---|---|---|---|
| 2013/0309689 A1* | 11/2013 | Rogers ................... | G01N 33/58 436/501 |
| 2019/0144689 A1 | 5/2019 | Yamada et al. | |
| 2019/0207137 A1 | 7/2019 | Mei | |

FOREIGN PATENT DOCUMENTS

| | | | |
|---|---|---|---|
| CN | 105449111 | * | 3/2016 |
| CN | 108129661 A | | 6/2018 |
| CN | 109456766 A | | 3/2019 |

OTHER PUBLICATIONS

Machine translation CN 105449111, Mar. 2016.*
Greene et al. Protective Groups in Organic Synthesis (p. 1-15) 1991.*
The State Intellectual Property Office of People's Republic of China. Chinese First Office Action dated Aug. 19, 2022. Chinese Patent Application No. 201910927985.5. Name of Applicant: Jing Oriental Technology Co., Ltd. English Language. 9 pages.
The State Intellectual Property Office of People's Republic of China. Chinese First Office Action dated Aug. 19, 2022. Chinese Patent Application No. 201910927985.5. Name of Applicant: Jing Oriental Technology Co., Ltd. Chinese Language. 7 pages.

* cited by examiner

*Primary Examiner* — Ana Z Muresan
(74) *Attorney, Agent, or Firm* — Procopio, Cory, Hargreaves & Savitch LLP

(57) ABSTRACT

A ligand includes a molecular skeleton, a first coordinating group connected to the molecular skeleton, at least one initial group connected to the molecular skeleton, and a protecting group connected to an end of each initial group away from the molecular skeleton. Each initial group is capable of forming a second coordinating group after deprotection.

8 Claims, 16 Drawing Sheets

LIGAND AND METHOD OF MANUFACTURING THE SAME, QUANTUM DOT FILM AND METHOD OF MANUFACTURING THE SAME, AND DISPLAY APPARATUS

CROSS-REFERENCE TO RELATED APPLICATION

This application claims priority to Chinese Patent Application No. 201910927985.5, filed on Sep. 27, 2019, which is incorporated herein by reference in its entirety.

TECHNICAL FIELD

The present disclosure relates to the field of display technologies, and in particular, to a ligand and a method of manufacturing the same, a quantum dot film and a method of manufacturing the same, and a display apparatus.

BACKGROUND

Quantum dots are semiconductor nanocrystals with unique light-emitting properties, such as a wide excitation peak, a narrow emission peak, and an adjustable luminescent spectrum, which are widely used in the field of photoelectric technologies. A quantum dot light-emitting diode (QLED) has advantages of a large color gamut and a fast response speed due to that there are a plurality of quantum dots dispersed in a light-emitting layer in the QLED. The application of the QLED to a display apparatus may make the display apparatus also have the above advantages, thereby attracting much attention.

The quantum dots are easy to agglomerate together because of their small sizes and large specific surface areas. In addition, the quantum dots have many surface defects. Therefore, a ligand needs to be formed on a surface of the quantum dot in a process of manufacturing a structure (such as the light-emitting layer) containing the quantum dots. By using of the ligand, the dispersive capability and luminescence performance of the quantum dots may be increased, and the surface defects of the quantum dots may be passivated.

SUMMARY

In first aspect, some embodiments of the present disclosure provide a ligand. The ligand includes a molecular skeleton, a first coordinating group connected to the molecular skeleton, at least one initial group connected to the molecular skeleton, and a protecting group connected to an end of each initial group away from the molecular skeleton. Each initial group is capable of forming a second coordinating group after deprotection.

In some embodiments, for a same central atom, a coordination capability of the second coordinating group to the central atom is stronger than a coordination capability of the first coordinating group to the central atom.

In some embodiments, the first coordinating group includes one of an amino group, an imino group, a carboxyl group, or a sulfhydryl group. In some other embodiments, the second coordinating group formed after each initial group is deprotected includes one of an amino group, an imino group, a carboxyl group, or a sulfhydryl group. In some other embodiments, the first coordinating group includes one of an amino group, an imino group, a carboxyl group or a sulfhydryl group, and the second coordinating group formed after each initial group is deprotected includes one of an amino group, an imino group, a carboxyl group, or a sulfhydryl group.

In some embodiments, a decomposable bond formed between each initial group and the protecting group includes a photolytic chemical bond or a pyrolytic chemical bond. The photolytic chemical bond is capable of being broken under ultraviolet (UV) light irradiation. The pyrolytic chemical bond is capable of being broken by heating.

In some embodiments, the photolytic chemical bond includes at least one of an azo bond, a peroxy bond, an acetophenone bond, a disulfide bond, or an episulfide bond. The pyrolytic chemical bond includes at least one of an amide bond, an ester bond, or an ether bond.

In some embodiments, a group of the molecular skeleton includes at least one of an ester bond, an ether bond, or a ketone bond.

In some embodiments, the molecular skeleton includes a linear chain molecular skeleton or a dendritic molecular skeleton.

In some embodiments, the molecular skeleton includes the linear chain molecular skeleton. The first coordinating group is connected to one end of the linear chain molecular skeleton, and the at least one initial group is connected to the other end of the linear chain molecular skeleton. In some other embodiments, the molecular skeleton includes the dendritic molecular skeleton, and the dendritic molecular skeleton includes a core and a plurality of branching units connected to the core. The first coordinating group is connected to the core, and the at least one initial group includes a plurality of initial groups each connected to an end of a corresponding one of the plurality of branching units away from the core.

In some embodiments, the molecular skeleton includes a molecular skeleton capable of transporting holes or a molecular skeleton capable of transporting electrons.

In some embodiments, the molecular skeleton capable of transporting holes includes one of a triphenylamine molecular skeleton, a carbazole molecular skeleton, or a fluorene molecular skeleton. The molecular skeleton capable of transporting electrons includes one of a pyridine molecular skeleton, a naphthalene molecular skeleton or a triazole molecular skeleton.

In some embodiments, the ligand further includes an intermediate skeleton connected to the molecular skeleton. The at least one initial group is connected to an end of the molecular skeleton through the intermediate skeleton, and the first coordinating group is directly connected to the molecular skeleton. Or both the first coordinating group and the at least one initial group are connected to the molecular skeleton through the intermediate skeleton.

In some embodiments, the intermediate skeleton includes a linear chain intermediate skeleton or a dendritic intermediate skeleton.

In second aspect, some embodiments of the present disclosure provide a method of manufacturing the ligand provided by the above embodiments. The method include: performing a reaction between a first compound containing the first coordinating group and a second compound containing the at least one initial group and the protecting group connected to each initial group, so as to obtain the ligand.

In third aspect, some embodiments of the present disclosure provide a quantum dot film. The quantum dot film includes a plurality of quantum dots, and a ligand coordinated with at least one of the plurality of quantum dots. The ligand is the ligand provided by the above embodiments, including at least one second coordinating group correspondingly formed after the at least one initial group is deprotected.

In fourth aspect, some embodiments of the present disclosure provide a display apparatus. The display apparatus includes a base substrate, and a quantum dot light-emitting device disposed on the base substrate. The quantum dot light-emitting device includes the quantum dot film provided by the above embodiments.

In fifth aspect, some embodiments of the present disclosure provide a method of manufacturing a quantum dot film. The method includes: performing a coordination reaction between the ligand provided by the above embodiments and a quantum dot of a plurality quantum dots, so as to obtain a preformed coordination solution; forming a preformed film by using of the preformed coordination solution; and processing the preformed film, so as to make the protecting group in the ligand in the preformed film be detached from each initial group to form the second coordinating group. The second coordinating group is coordinated with the quantum dot or another of the plurality quantum dots.

In some embodiments, performing the coordination reaction between the ligand and the quantum dot, so as to obtain the preformed coordination solution, includes: performing a coordination reaction between the ligand and the quantum dot directly, so as to obtain the preformed coordination solution. In some other embodiments, performing the coordination reaction between the ligand and the quantum dot, so as to obtain the preformed coordination solution, includes: providing a quantum dot coordinated with a pre-ligand; and performing a ligand interchange reaction between the ligand and the quantum dot coordinated with the pre-ligand, so as to obtain the preformed coordination solution. For a same central atom on a surface of the quantum dot coordinated with the pre-ligand, a coordination capability of the pre-ligand to the central atom is weaker than a coordination capability of the first coordinating group to the central atom.

In some embodiments, processing the preformed film, so as to make the protecting group in the ligand in the preformed film be detached from each initial group, includes irradiating the preformed film by using of UV light or heating the preformed film, so as to make the protecting group in the ligand in the preformed film be detached from each initial group.

In some embodiments, after the preformed film is processed, the method further includes: adding methanol to the preformed film to dissolve at least one of the detached protecting group or sub-groups decomposed from the detached protecting group; and removing the methanol.

BRIEF DESCRIPTION OF THE DRAWINGS

In order to describe technical solutions in the present disclosure more clearly, accompanying drawings to be used in some embodiments of the present disclosure will be introduced briefly. However, the accompanying drawings to be described below are merely accompanying drawings of some embodiments of the present disclosure, and a person of ordinary skill in the art may obtain other drawings according to these drawings. In addition, the accompanying drawings in the following description may be regarded as schematic diagrams, and are not limitations on actual sizes of products, actual processes of methods and actual timings of signals that the embodiments of the present disclosure relate to.

DETAILED DESCRIPTION

Figure 1:
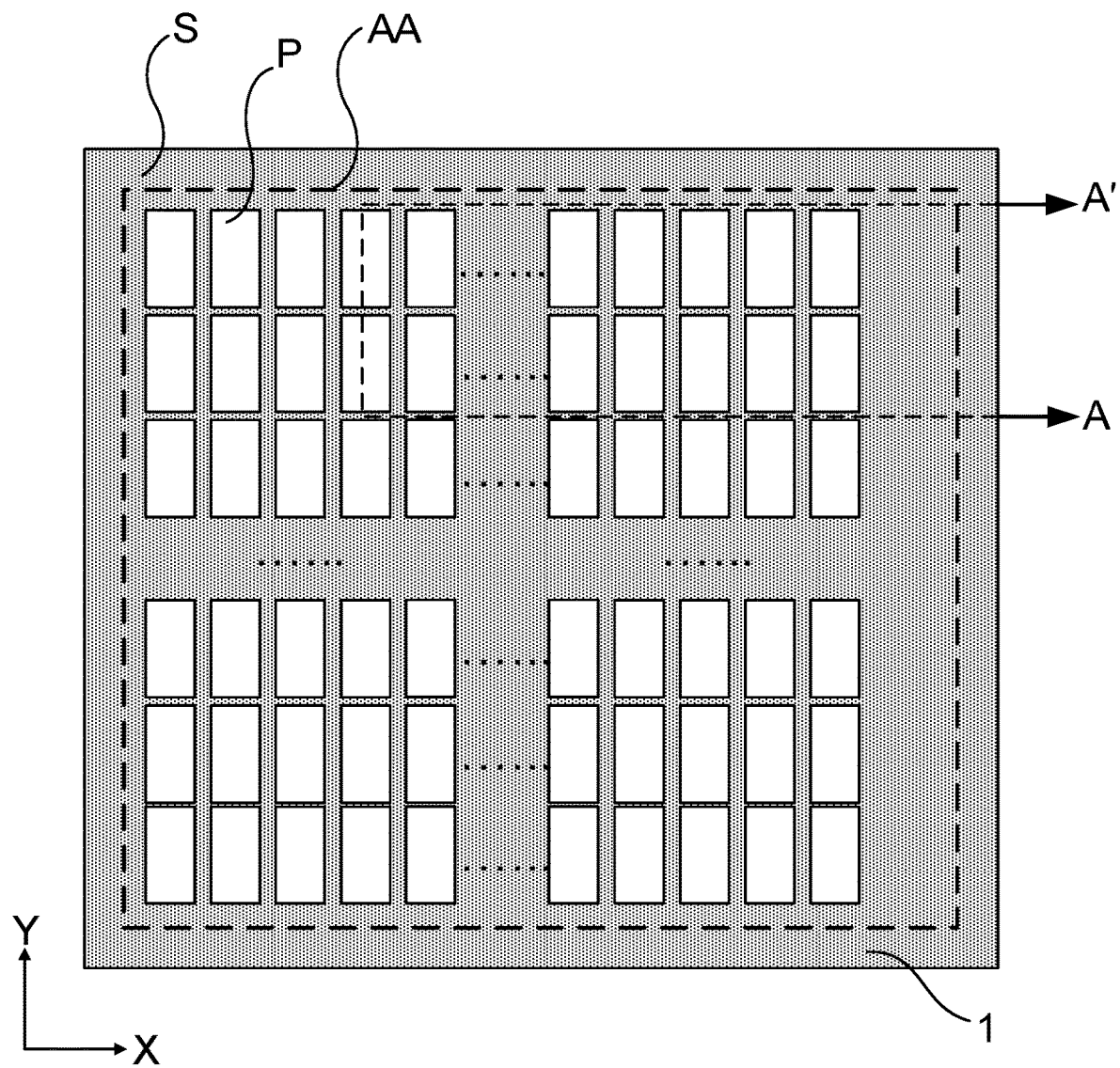
FIG. 1 is a top view of a display apparatus, in accordance with some embodiments.

Technical solutions in some embodiments of the present disclosure will be described clearly and completely with reference to accompanying drawings. However, the described embodiments are merely some but not all of embodiments of the present disclosure. All other embodiments obtained on a basis of the embodiments of the present disclosure by a person of ordinary skill in the art shall be included in the protection scope of the present disclosure.

Unless the context requires otherwise, throughout the Description and the appended claims, terms "comprise" and other forms thereof such as the third-person singular form "comprises" and the present participle form "comprising" are construed as an open-ended and inclusive meaning, i.e., "included, but not limited to". In the description of the Description, terms such as "one embodiment", "some embodiments", "exemplary embodiments", "example", "specific example" or "some examples" are intended to indicate that specific features, structures, materials or characteristics related to the embodiment(s) or example(s) are included in at least one embodiment or example of the present disclosure. Schematic representations of the above terms do not necessarily refer to the same embodiment(s) or example(s). In addition, the specific features, structures, materials or characteristics may be included in any one or more embodiments/examples in any suitable manner.

Hereinafter, terms such as "first" and "second" are only used for descriptive purposes, and are not to be construed as indicating or implying the relative importance or implicitly indicating the number of indicated technical features below. Thus, features defined as "first" and "second" may explicitly or implicitly include one or more of the features. As used in the Description and the claims, the singular forms "a", "an", and "the" include plural referents unless the content clearly dictates otherwise. In the description of the embodiments of the present disclosure, term "a/the plurality of" means two or more unless otherwise specified.

In the description of some embodiments, terms such as "connected" and its extensions may be used. For example, term "connected" may be used in the description of some embodiments to indicate that two or more objects are in direct physical, chemical, or electrical contact with each other. The embodiments disclosed herein are not necessarily limited to the contents herein.

"At least one of A, B and C" has the same meaning as "at least one of A, B or C", and both include the following combinations of A, B and C: only A, only B, only C, a combination of A and B, a combination of A and C, a combination of B and C, and a combination of A, B and C. Similarly, "A and/or B" includes the following three combinations: only A, only B, and a combination of A and B.

The use of terms "adapted to" or "configured to" herein is meant as open and inclusive that does not foreclose devices adapted to or configured to perform additional tasks or steps.

Exemplary embodiments are described herein with reference to sectional views and/or plan views as idealized exemplary drawings. In the drawings, thicknesses of layers and regions may be exaggerated for clarity. Accordingly, variations in shape relative to the drawings due to, for example, manufacturing techniques and/or tolerances may be envisaged. Therefore, exemplary embodiments should not be construed as being limited to the shapes of the regions shown herein, but include deviations in shape due to, for example, manufacturing. Therefore, the regions illustrated in the drawings are schematic in nature and their shapes are not intended to illustrate actual shapes of regions in a device and are not intended to limit the scope of the exemplary embodiments.

It will also be understood that when a layer or element is referred to as being "on" another layer or substrate, it may be directly on the another layer or the substrate, or one or more intervening layers or elements may also be present.

Some embodiments of the present disclosure provide a display apparatus. FIG. 1 is a top view of an illustrative display apparatus. As shown in FIG. 1, the display apparatus 1 has an active area (i.e., display area) AA.

As shown in FIG. 1, the active area AA is provided with a plurality of sub-pixels P (such as red sub-pixels, green sub-pixels, and blue sub-pixels) therein. In some examples, as shown in FIG. 1, the plurality of sub-pixels P are arranged in a matrix. In this case, sub-pixels P arranged in a same line in a horizontal direction X (i.e., a row direction) are referred to as sub-pixels in a same row, and sub-pixels P arranged in a same line in a vertical direction Y (i.e., a column direction) are referred to as sub-pixels in a same column. The sub-pixels P in the same row may be connected to a same gate line, and the sub-pixels P in the same column may be connected to a same data line.

It will be understood that the plurality of sub-pixels P arranged in the matrix in FIG. 1 is only for illustration. In some other examples, in the plurality of sub-pixels P, sub-pixels P in all odd-numbered rows are arranged in a same matrix, and sub-pixels P in all even-numbered rows are arranged in a same matrix. Moreover, in any two adjacent rows, one sub-pixel P in an odd-numbered row directly faces a gap between two sub-pixels P that are in an even-numbered row and adjacent to the one sub-pixel P. That is, one sub-pixel P in an odd-numbered row and two sub-pixels P that are in an even-numbered row and adjacent to the one sub-pixel P are arranged in a Delta (i.e., Δ) shape.

As shown in FIG. 1, in some examples, the display apparatus 1 further has a peripheral area (i.e., non-active area or non-display area) S outside the active area AA. The peripheral area S is provided with a circuit structure electrically connected to some conductive structures in the active area AA therein. For example, the circuit structure includes a plurality of traces (such as at least one of a lead wire for connecting a gate line in the active area AA, a lead wire for connecting a data line in the active area AA, a lead wire for connecting a common electrode in the active area AA, or a power line), a plurality of bonding electrodes, and at least one driver circuit (such as at least one of a gate driver circuit or a source driver circuit).

The structures in the peripheral area S should be adjusted accordingly on the basis of the specific design of the display apparatus 1. The above description is only an example, which is not limited by the embodiments of the present disclosure. In addition, the specific position of the peripheral area S outside the active area AA may be changed according to different designs of the display apparatus 1. For example, the peripheral area S surrounds the active area AA. Or, the peripheral area S is located at one or more sides of the periphery of the active area AA, but does not surround the active area AA, which is not limited by the embodiments of the present disclosure.

Figure 2:
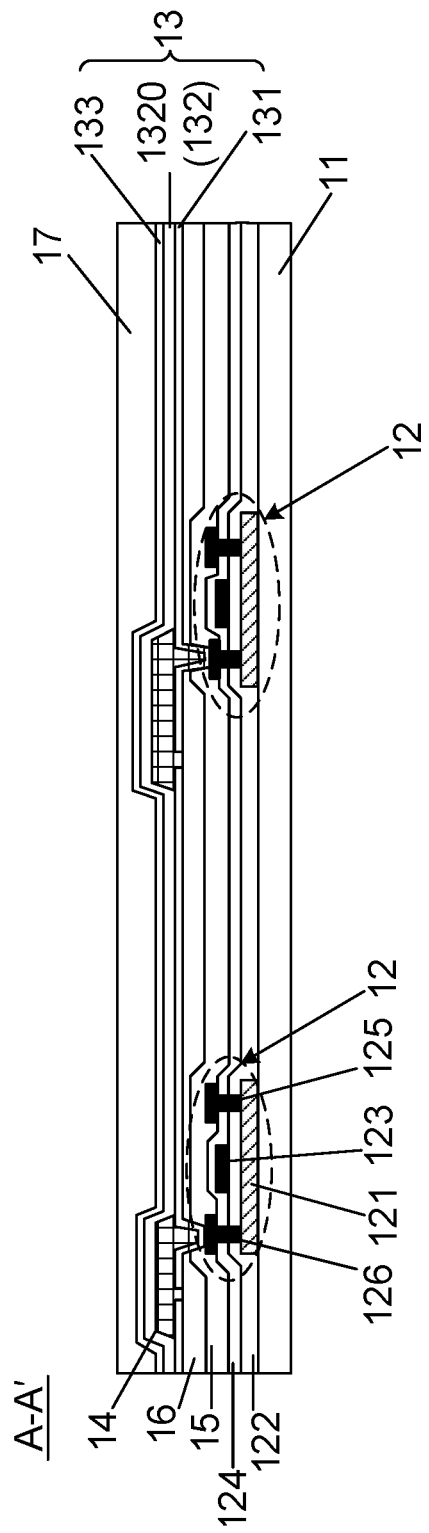
FIG. 2 is a sectional view of a display apparatus along direction A-A' in FIG. 1, in accordance with some embodiments.

FIG. 2 is a sectional view of the display apparatus along the direction A-A' in FIG. 1. As shown in FIG. 2, the display apparatus 1 includes a base substrate 11. The plurality of sub-pixels P are disposed on the base substrate 11. Each sub-pixel P includes a pixel driver circuit and a light-emitting device 13. The pixel driver circuit includes a plurality of transistors (e.g., thin film transistors, (TFTs)). One of the transistors is a driving transistor 12, and at least one of the remaining transistors is a switching transistor. Herein, the driving transistor is used to drive the light-emitting device to emit light (e.g., red light, green light, or blue light). Typically, a width-to-length ratio of the channel of the driving transistor is greater than a width-to-length ratio of the channel of the switching transistor.

In some examples, as shown in FIG. 2, the driving transistor 12 includes an active pattern 121, a gate 123, a first electrode 125 and a second electrode 126 that are sequentially stacked on top of one another on the base substrate 11. The first electrode 125 and the second electrode 126 are disposed in a same layer. As shown in FIG. 2, in some examples, the display apparatus 1 further includes a gate insulating layer 122 for isolating the active pattern 121 from the gate 123, and an interlayer insulating layer 124 for isolating the gate 123 from the first electrode 125 and the second electrode 126.

It will be noted that the first electrode 125 is one of a source and a drain of the driving transistor 12, and the second electrode 126 is the other one of the source and the drain of the driving transistor 12. Since the source and the drain of the transistor may be symmetrical in structure, there may be no difference in structure between the source and the drain of the transistor. That is, there may be no difference in structure between the first electrode 125 and the second electrode 126 of the driving transistor in the embodiments of the present disclosure. For example, as shown in FIG. 2, the second electrode 126 is the drain of the driving transistor 12, and is electrically connected to a first electrode 131 of the light-emitting device 13 to drive the light-emitting device 13 to emit light.

As shown in FIG. 2, in some examples, the display apparatus 1 further includes a pixel defining layer 14. The pixel defining layer 14 includes a plurality of openings, and the light-emitting device 13 is disposed in an opening. As shown in FIG. 2, it will be understood that the light-emitting device 13 further includes a light-emitting functional layer 132 and a second electrode 133. In some examples, the light-emitting functional layer 132 includes a light-emitting layer 1320. In some other examples, the light-emitting functional layer 132 includes a light-emitting layer 1320, and at least one of an electron transport layer (ETL), an electron injection layer (EIL), a hole transport layer (HTL) or a hole injection layer (HIL).

The light-emitting device 13 may be a top emission type light-emitting device, a bottom emission type light-emitting device, or a double emission type light-emitting device. Regardless of whether the light-emitting device 13 is a top emission type light-emitting device, a bottom emission type light-emitting device, or a double emission type light-emitting device, in a case where the first electrode 131 is an anode, the second electrode 133 is a cathode; and in a case where the first electrode 131 is a cathode, the second electrode 133 is an anode.

Herein, in an example where the light-emitting device 13 is a top emission type light-emitting device, the first electrode 131 may be an anode. In this case, the first electrode 131 is opaque, such as a stacked structure composed of a layer of indium tin oxides (ITO), a layer of silver (Ag), and a layer of ITO (i.e., an ITO/Ag/ITO structure). In this way, a part of light emitted from the light-emitting layer 1320 that is emitted toward the first electrode 131 is reflected, which improves the light extraction rate of the light-emitting device 13. Accordingly, the second electrode 133 is a cathode. In this case, the second electrode 133 is transparent or translucent, such as a thin layer of silver, to transmit the light emitted from the light-emitting layer 1320.

In addition, as shown in FIG. 2, the display apparatus further includes, for example, a passivation layer 15 and a planarization layer 16 that are disposed between the driving transistor 12 and the first electrode 131, so as to space the first electrode 131 apart from structures below. Moreover, the passivation layer 15 and the planarization layer 16 may provide a flat base substrate for the first electrode 131, thereby facilitating the manufacturing of the first electrode 13.

Based on this, the display apparatus further includes an encapsulation structure 17 for encapsulating the light-emitting device 13. For example, the encapsulation structure 17 may be an encapsulation film. Or, the encapsulation structure 17 may be an encapsulation substrate.

Some embodiments of the present disclosure provide a quantum dot film, which may serve as the light-emitting layer 1320 in the light-emitting device 13 provided by the above embodiments. That is, the display apparatus 1 provided by the above embodiments is a QLED display apparatus, and the light-emitting device 13 in the display apparatus 1 is a quantum dot light-emitting device. Of course, the quantum dot film may also serve as a structure in other devices, such as a color film, the embodiments of the present disclosure do not limit thereto.

Figure 20:
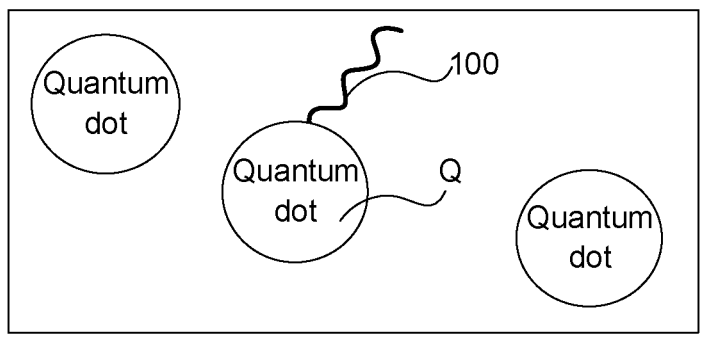
FIG. 20 is a structural diagram of a quantum dot film, in accordance with some embodiments.

A structure of an illustrative quantum dot film is shown in FIG. 20. As shown in FIG. 20, the quantum dot film 1000 includes a plurality of quantum dots Q and a ligand 100 coordinated with at least one of the plurality of quantum dots Q. In some examples, the quantum dot film 1000 includes a plurality of ligands 100 coordinated with the quantum dots Q. One quantum dot Q may be coordinated with one ligand 100, or, one quantum dot Q may be coordinated with some of the ligands 100. Similarly, one ligand 100 may be coordinated with one quantum dot Q, or, one ligand 100 may be coordinated with some of the quantum dots Q.

Figure 3:
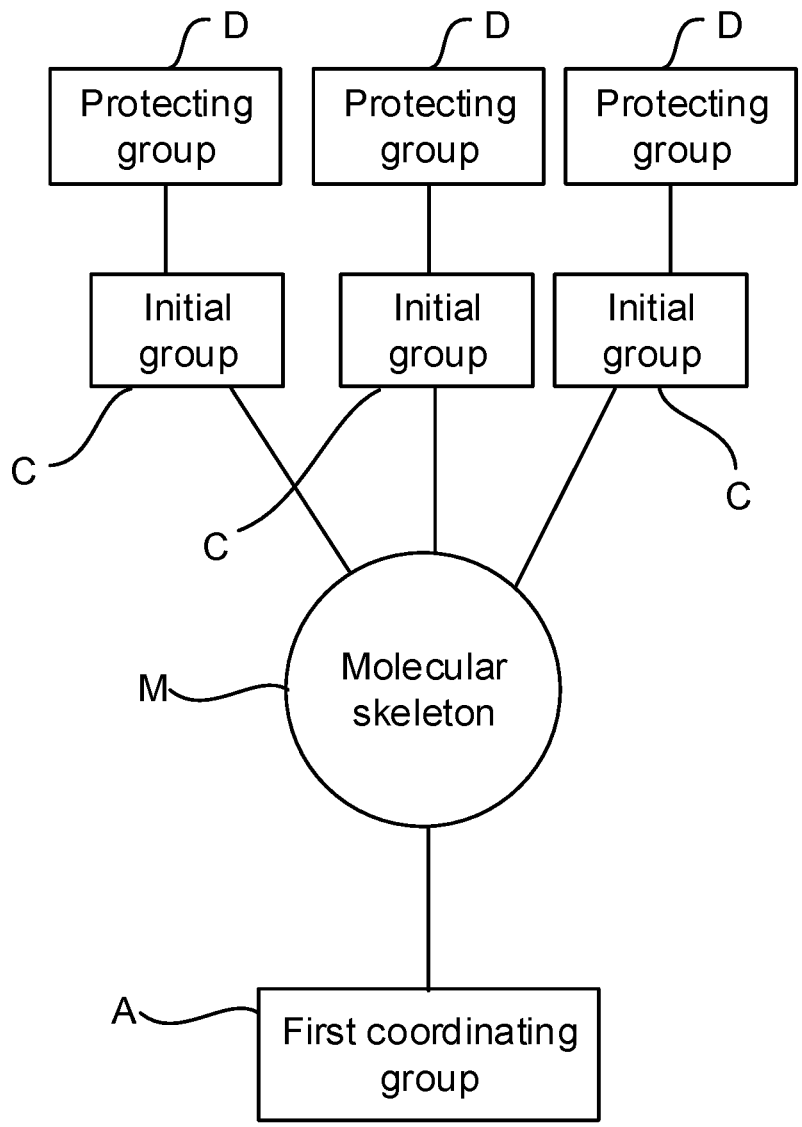
FIG. 3 is a structural diagram of a ligand, in accordance with some embodiments.
Figure 4:
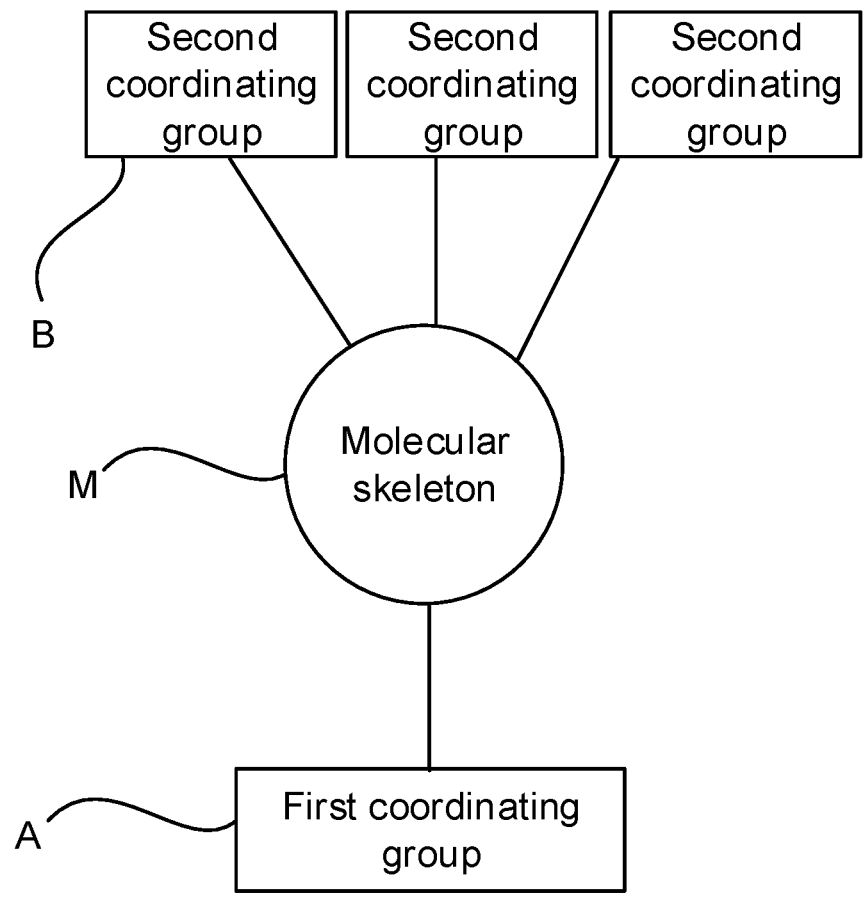
FIG. 4 is a structural diagram of the ligand shown in FIG. 3 having a second coordinating group formed after an initial group is deprotected, in accordance with some embodiments.

A structure of an illustrative ligand is shown in FIG. 3. As shown in FIG. 3, the ligand 100 includes a molecular skeleton M, a first coordinating group A connected to the molecular skeleton M, at least one initial group C connected to the molecular skeleton M, and a protecting group D connected to an end of each initial group C away from the molecular skeleton M. A structure of the ligand in which the initial group C is deprotected is shown in FIG. 4. As shown in FIG. 4, each initial group C is capable of forming a second coordinating group B after deprotection.

For example, as shown in FIG. 3, the initial group C is connected to the protecting group D. The protecting group D is configured to protect the initial group C connected thereto, so that the initial group C is not coordinated with the quantum dot. The second coordinating group B is formed after the initial group C is deprotected (that is, the protecting group D is detached from the initial group C), and the second coordinating group B is capable of being coordinated with the quantum dot.

Figure 5:
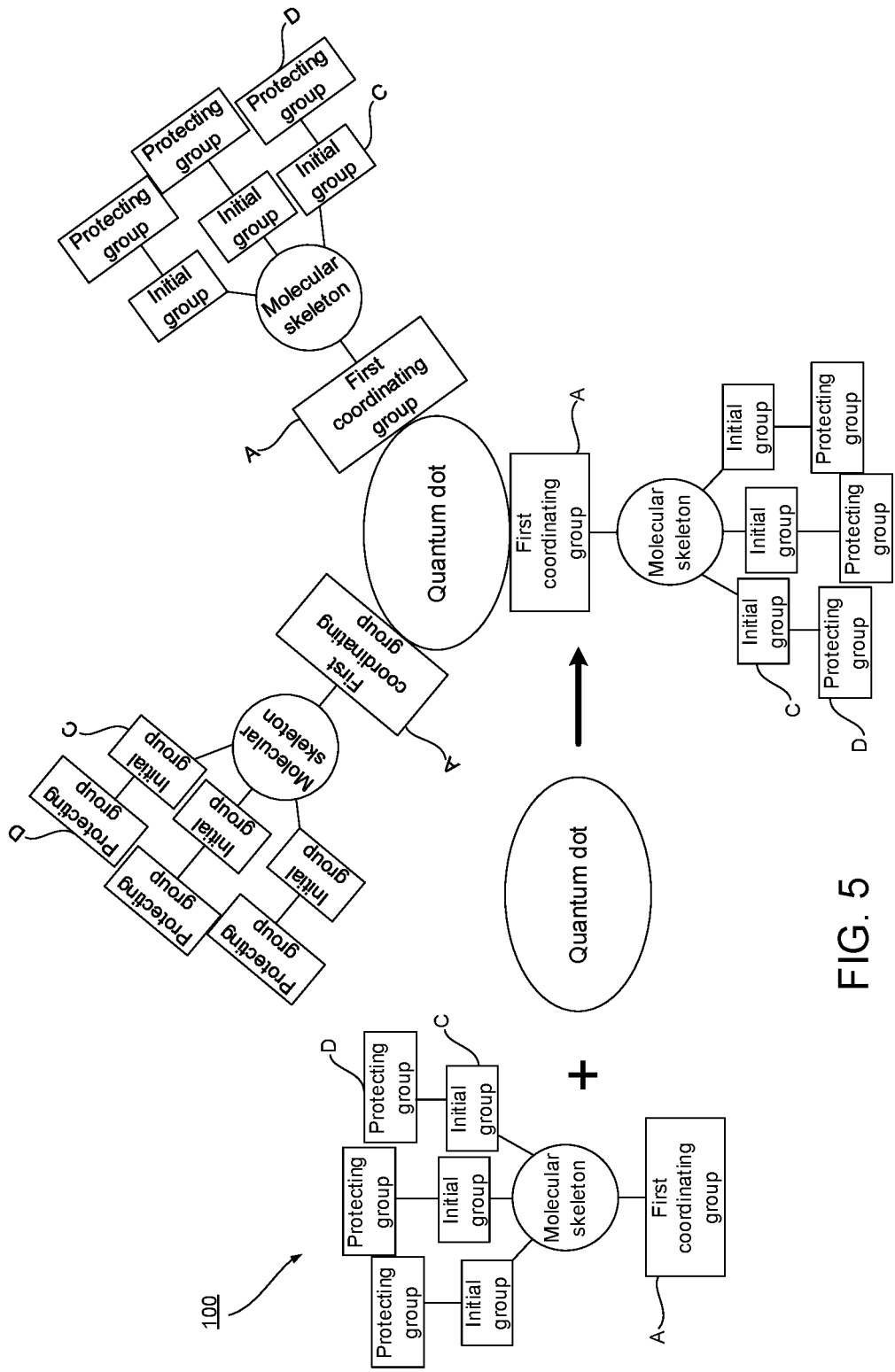
FIG. 5 is a diagram showing a process in which a ligand and a quantum dot are coordinated to form a coordination compound, in accordance with some embodiments.
Figure 6:
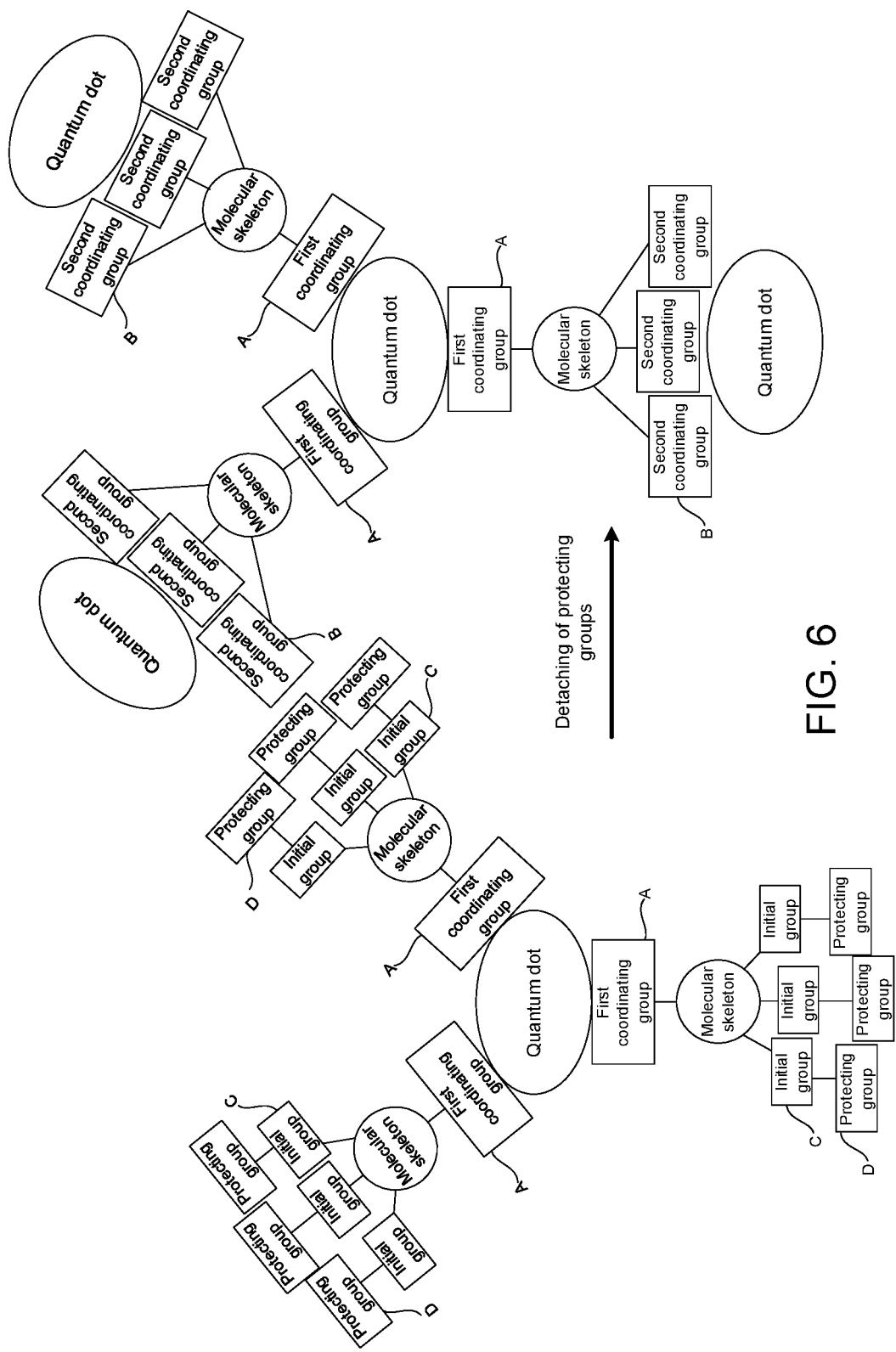
FIG. 6 is a diagram showing a process in which the coordination compound in FIG. 5 whose protecting groups are detached is coordinated with other quantum dots, in accordance with some embodiments.

An illustrative process in which the ligand 100 and the quantum dot are coordinated to form a coordination compound is shown in FIG. 5, and an illustrative process in which the coordination compound in FIG. 5 whose protecting groups D are detached is coordinated with other quantum dots is shown in FIG. 6. As shown in FIG. 5, the first coordinating group A in the ligand 100 is first coordinated with the quantum dot, and then (for example, after a quantum dot film is formed), as shown in FIG. 6, the ligand 100 is processed, so that the protecting groups D are detached from the initial groups C. Therefore, the second coordinating groups B are formed after the initial groups C are deprotected. In this way, there may be a plurality of coordinating groups in a single ligand 100, and each second coordinating group B formed after deprotection may be coordinated with the quantum dots around it. Therefore, a stable chelate or a structure similar to chelate (i.e., an annular structure) may be formed.

In some other examples, in a same ligand 100, the first coordinating group A in the ligand 100 is first coordinated with one quantum dot, and then the protecting group D is detached from the initial group C to form a second coordinating group B. The second coordinating group B may continue to be coordinated with the same quantum dot. That is, after the protecting group D in the ligand 100 is detached, the first coordinating group A and the second coordinating group B in the same ligand 100 may be coordinated with the same quantum dot.

It will be understood that the ordinal number "first" in the first coordinating group A and the ordinal number "second" in the second coordinating group B are only for explaining that the first coordinating group A may be different from the second coordinating group B formed after the initial group C is deprotected. That is, after the initial group C in the ligand 100 is deprotected, the ligand 100 may include a plurality of coordinating groups with different types. The different ordinal numbers do not limit the coordination capabilities of the first coordinating group A and the second coordinating group B. That is, for a same central atom (that is, a same metal atom on a surface of a quantum dot to be coordinated with the ligand 100 or same metal atoms on surfaces of quantum dots to be coordinated with the ligand 100), the coordination capability of the first coordinating group A to the central atom may be stronger than, equal to or weaker than the coordination capability of the second coordinating group B to the central atom.

In some embodiments, the first coordinating group A may include a group containing lone pair electrons, for example, one of an amino group (—NH$_2$), an imino group (═NH), a carboxyl group (—COOH) or a sulfhydryl group (—SH).

In some embodiments, the second coordinating group B formed after the initial group C is deprotected may include a group containing lone pair electrons, for example, one of an amino group (—NH$_2$), an imino group (═NH), a carboxyl group (—COOH) or a sulfhydryl group (—SH).

In some other embodiments, the first coordinating group includes one of an amino group (—NH$_2$), an imino group (═NH), a carboxyl group (—COOH) or a sulfhydryl group (—SH), and the second coordinating group B formed after the initial group C is deprotected includes one of an amino group (—NH$_2$), an imino group (═NH), a carboxyl group (—COOH) or a sulfhydryl group (—SH).

Some embodiments of the present disclosure do not limit the types of the first coordinating group A and the second coordinating group B formed after the initial group C is deprotected. In some examples, the first coordinating group A and the second coordinating group B are different types of coordinating groups. Herein, the phrase "different types" means that: as long as the first coordinating group A and the second coordinating group B meet any one of the following conditions, the first coordinating group A and the second coordinating group B may be considered as different types of coordinating groups.

In a first condition, atoms containing lone pair electrons used for coordinating in the first coordinating group A and the second coordinating group B are different. For example, the first coordinating group A is an amino group (—NH$_2$). That is, the atom containing lone pair electrons is a nitrogen (N) atom. The second coordinating group B is a carboxyl group (—COON) or a sulfhydryl group (—SH). That is, the atom containing lone pair electrons is an oxygen (O) atom or a sulfur (S) atom.

In a second condition, the atoms containing lone pair electrons used for coordinating in the first coordinating group A and the second coordinating group B are the same. For a same central atom, a coordination capability of the first coordinating group A to the central atom and a coordination capability of the second coordinating group B to the central atom are different. For example, the first coordinating group A is an amino group (—NH$_2$), and the second coordinating group B is an imino group (═NH). That is, the atoms containing lone pair electrons of the first coordinating group A and the second coordinating group B are both nitrogen (N) atoms.

That is, in some examples, the first coordinating group A may include a group containing lone pair electrons, such as one of the amino group, the imino group, the carboxyl group, or the sulfhydryl group. The second coordinating group B formed after the initial group C is deprotected may include a group containing lone pair electrons, such as at least one of the amino group, the imino group, the carboxyl group or the sulfhydryl group. In this case, the one of the amino group, the imino group, the carboxyl group or the sulfhydryl group, included in the first coordinating group A, is different from the one of the amino group, the imino group, the carboxyl group or the sulfhydryl group that is included in the second coordinating group B formed after the initial group C is deprotected.

In some embodiments, the at least one initial group C includes a plurality of initial groups C. That is, there are a plurality of second coordinating groups B correspondingly formed after the plurality of initial groups C in the ligand 100 are deprotected. In some examples, each second coordinating group B may be the same. In other examples, each second coordinating group B may be different. That is, the plurality of second coordinating groups B include a plurality of types of second coordinating groups B, which is not limited by embodiments of the present disclosure. It will be understood that, in a case where each second coordinating group B is different, any one of the second coordinating groups B may be different from the first coordinating group A.

In the related art, a ligand including a coordinating group may only provide one coordination site to be coordinated with the quantum dot, and the ligand is coordinated with the quantum dot through a coordinate bond. Since the coordinate bond has a weak force, the coordinating group is easily desorbed from the surface of the quantum dot. That is, the ligand is easily detached from the surface of the quantum dot.

Compared with the related art, in the embodiments of the present disclosure, the first coordinating group A in the ligand 100 is first coordinated with the quantum dot. The initial group C is protected by the protecting group D and is not coordinated with the quantum dot. Then the protecting group D is detached from the initial group C to form the second coordinating group B, so that there are more coordinating groups in the ligand 100 to be coordinated with more quantum dots. Moreover, a problem of quantum dot agglomeration caused by the coordination of one ligand and a plurality of quantum dots will not occur. Therefore, the solubility of quantum dot is improved.

Based on this, the ligand 100 provided by the embodiments of the present disclosure may improve the solubility of the quantum dot, and the second coordinating group formed after the initial group C is deprotected may enable the ligand 100 to form a plurality of coordination sites to be coordinated with more quantum dots. Therefore, a chelate or a structure similar to chelate (i.e., an annular structure) may be formed, and the coordination capability between the ligand 100 and the quantum dots may be improved and the desorption may be prevented. Furthermore, it is possible to prevent the ligand 100 from detaching from the surface of the quantum dot and a large amount of surface defects from being exposed, and the passivation of the surface defects on the quantum dot is enhanced as well as the luminescence performance of the quantum dot is improved.

In some embodiments, for a same central atom, the coordination capability of the second coordinating group B to the central atom is stronger than the coordination capability of the first coordinating group A to the central atom. Therefore, by coordinating the second coordinating group B with the quantum dot, a combination capability between the ligand 100 and the quantum dot may be further enhanced to prevent the desorption.

Figure 7:
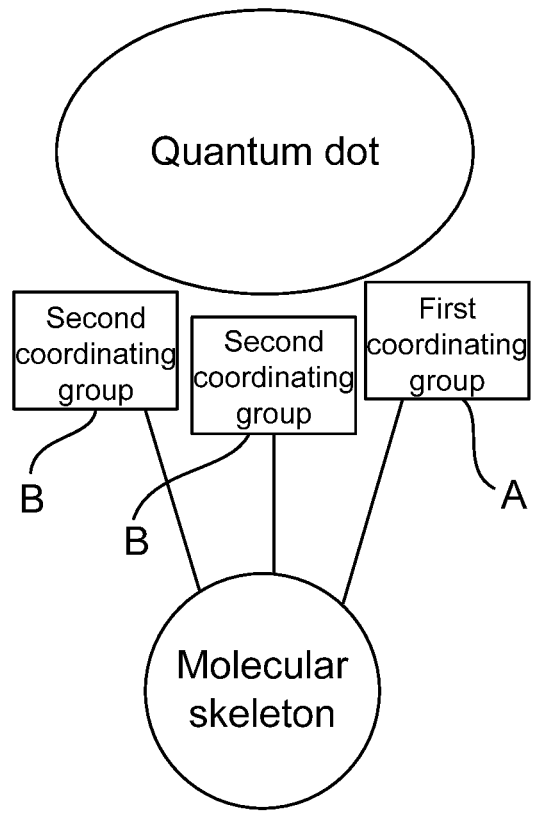
FIG. 7 is a structural diagram of a coordination compound formed by a coordination of a ligand and a quantum dot, in accordance with some embodiments.
Figure 8:
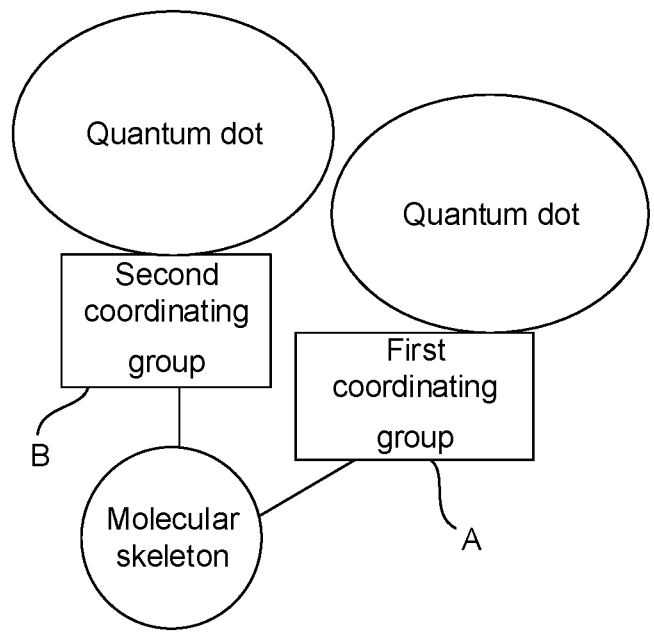
FIG. 8 is a structural diagram of another coordination compound formed by a coordination of a ligand and quantum dots, in accordance with some embodiments.
Figure 9:
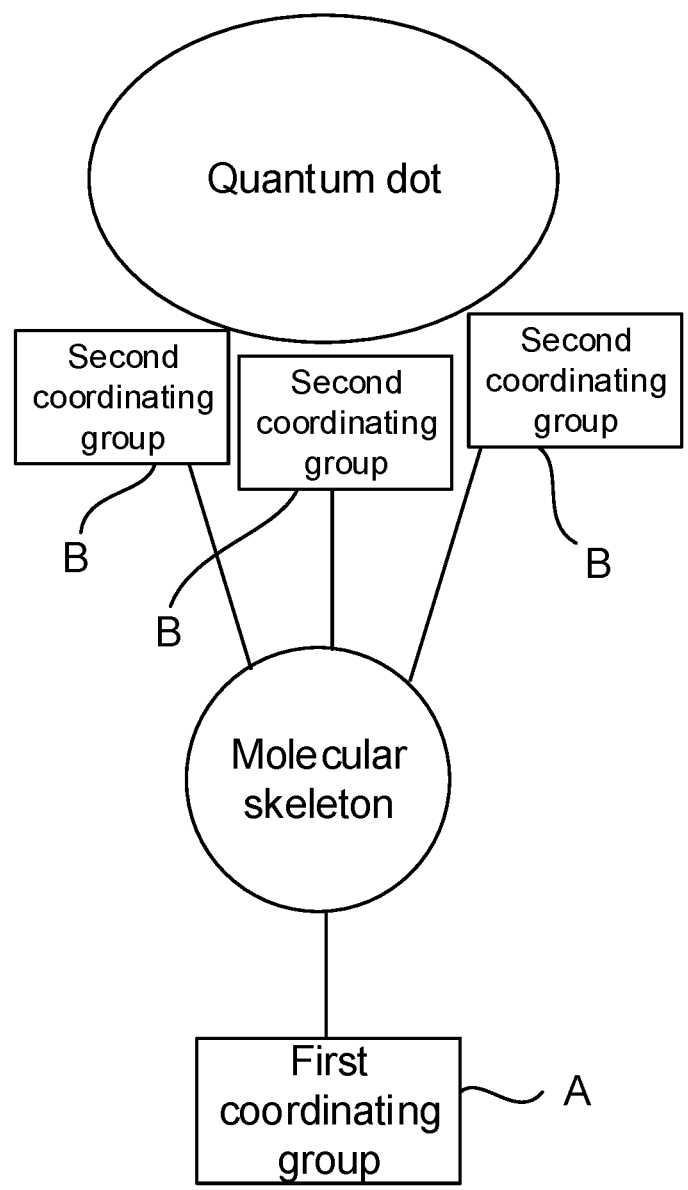
FIG. 9 is a structural diagram of yet another coordination compound formed by a coordination of a ligand and a quantum dot, in accordance with some embodiments.
Figure 10:
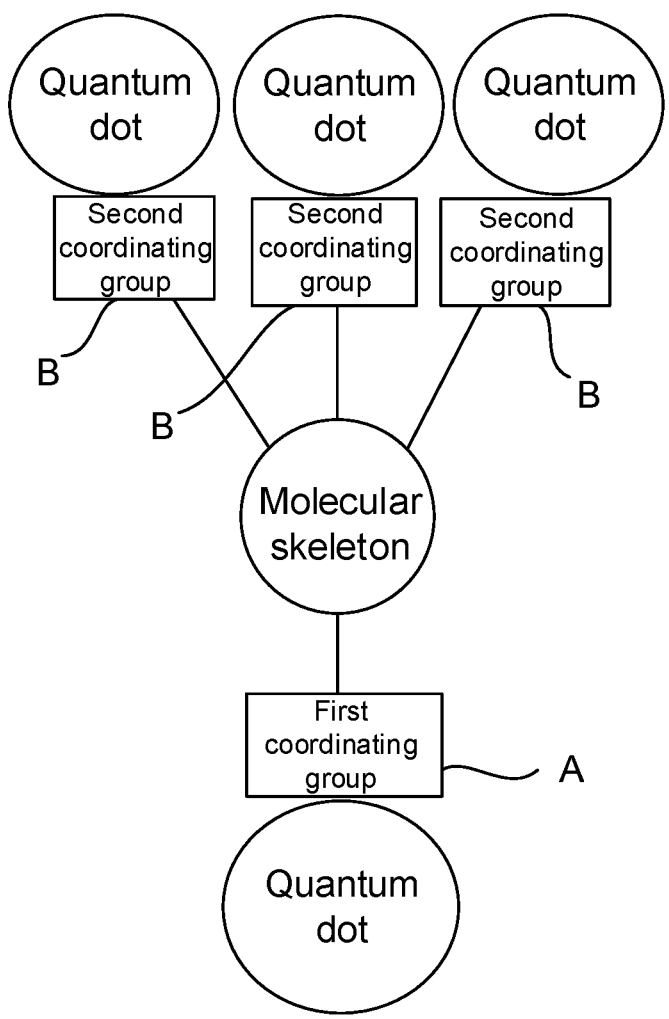
FIG. 10 is a structural diagram of yet another coordination compound formed by a coordination of a ligand and quantum dots, in accordance with some embodiments.

A structure of a coordination compound formed by a coordination of a ligand and a quantum dot is shown in FIG. 7, a structure of another coordination compound formed by a coordination of a ligand and quantum dots is shown in FIG. 8, a structure of yet another coordination compound formed by a coordination of a ligand and a quantum dot is shown in FIG. 9, and a structure of yet another coordination compound formed by a coordination of a ligand and quantum dots is shown in FIG. 10. As shown in FIGS. 7 to 10, in the ligand 100, the first coordinating group A and the second coordinating group B formed after the initial group C is deprotected may all be coordinated with at least one quantum dot.

For example, the ligand 100 includes one first coordinating group A and a plurality of initial groups C. As shown in FIG. 7, in the ligand 100, the first coordinating group A and a plurality of second coordinating groups B correspondingly formed after the plurality of initial groups C are deprotected are all coordinated with a same quantum dot.

Or, the ligand 100 includes one first coordinating group A and one initial group C. As shown in FIG. 8, in the ligand 100, the first coordinating group A and a second coordinating group B formed after the initial group C is deprotected are coordinated with different quantum dots.

Or, the ligand 100 includes one first coordinating group A and a plurality of initial groups C. As shown in FIG. 9, in the ligand 100, a plurality of second coordinating groups B correspondingly formed after the plurality of initial groups C are deprotected are coordinated with a same quantum dot.

Herein, for the same central atom, in the case where the coordination capability of the second coordinating group B (such as a sulfhydryl group) to the central atom is stronger than the coordination capability of the first coordinating group A (such as an amino group) to the central atom, as shown in FIG. 9, a quantum dot originally coordinated with the first coordinating group A in the ligand 100 may be coordinated with the plurality of second coordinating groups B. That is, FIG. 9 shows a case where the plurality of second coordinating groups B are coordinated with the same quantum dot, and the first coordinating group A is not coordinated with the quantum dot.

Or, the ligand 100 includes one first coordinating group A and a plurality of initial groups C. As shown in FIG. 10, in the ligand 100, the first coordinating group A is coordinated with one quantum dot, and a plurality of second coordinating groups B correspondingly formed after the plurality of initial group C are deprotected are coordinated with different quantum dots, respectively. That is, in the ligand 100, the first coordinating group A and the plurality of second coordinating groups B formed after the plurality of initial groups C are deprotected are all coordinated with different quantum dots.

In some embodiments of the present disclosure, the protecting group D may be a group that is capable of being detached from the initial group C under any suitable conditions, and loses its protective effect on the initial group C.

It will be understood that the protecting group D is capable of being detached from the initial group C, so that the second coordinating group B is formed after the initial group C is deprotected. That is, a decomposable bond may be formed between the protecting group D and the initial group C.

In some embodiments, the decomposable bond includes a photolytic chemical bond or a pyrolytic chemical bond. The photolytic chemical bond is capable of being broken under ultraviolet (UV) light irradiation, and the pyrolytic chemical bond is capable of being broken under heating.

That is, the protecting group D may be detached from the initial group C by UV light irradiation or heating, and the protective effect on the initial group C is lost. In this way, the second coordinating group B may be formed after the initial group C is deprotected.

For example, the photolytic chemical bond includes at least one of an azo bond, a peroxy bond, an acetophenone bond, a disulfide bond, or an episulfide bond. For example, the pyrolytic chemical bond includes at least one of an amide bond, an ester bond, or an ether bond.

Based on this, the embodiments of the present disclosure does not limit the structure of the molecular skeleton, as long as the first coordinating group A and the at least one initial group C can be connected to the molecular skeleton. Some examples are provided below to describe the above molecular skeleton in detail.

Figure 11:
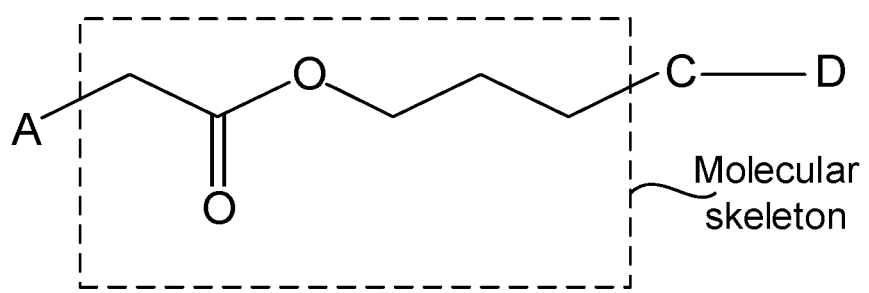
FIG. 11 is a structural diagram of another ligand, in accordance with some embodiments.
Figure 12:
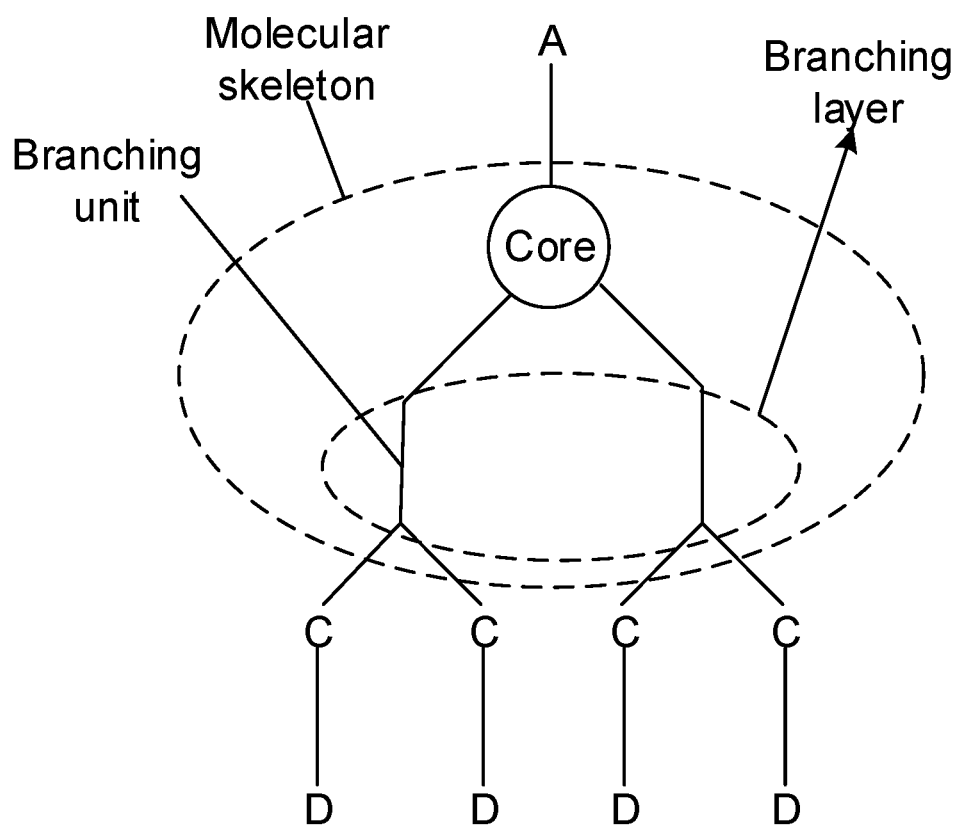
FIG. 12 is a structural diagram of yet another ligand, in accordance with some embodiments.

Structures of different ligands are shown in FIGS. 11 to 16. In some embodiments, the molecular skeleton includes a linear chain molecular skeleton (as shown in FIG. 11), or a dendritic molecular skeleton (as shown in FIG. 12).

In some embodiments, one group in the molecular skeleton may include at least one of an ester bond, an ether bond, or a ketone bond. The linear chain molecular skeleton may be a carbon chain molecular skeleton, such as an alkane molecular skeleton, an olefin molecular skeleton or an alkyne molecular skeleton.

FIG. 11 only shows an example in which the linear chain molecular skeleton is an alkane molecular skeleton. The alkane molecular skeleton may include at least one of the ester bond, the ether bond, or the ketone bond.

As shown in FIG. 12, the dendritic molecular skeleton refers to an organic molecular skeleton having a dendritic structure. The dendritic molecular skeleton is synthesized through repeated propagation reactions, and a branching layer is increased in each propagation reaction, referred to as a "generation".

Figure 13:
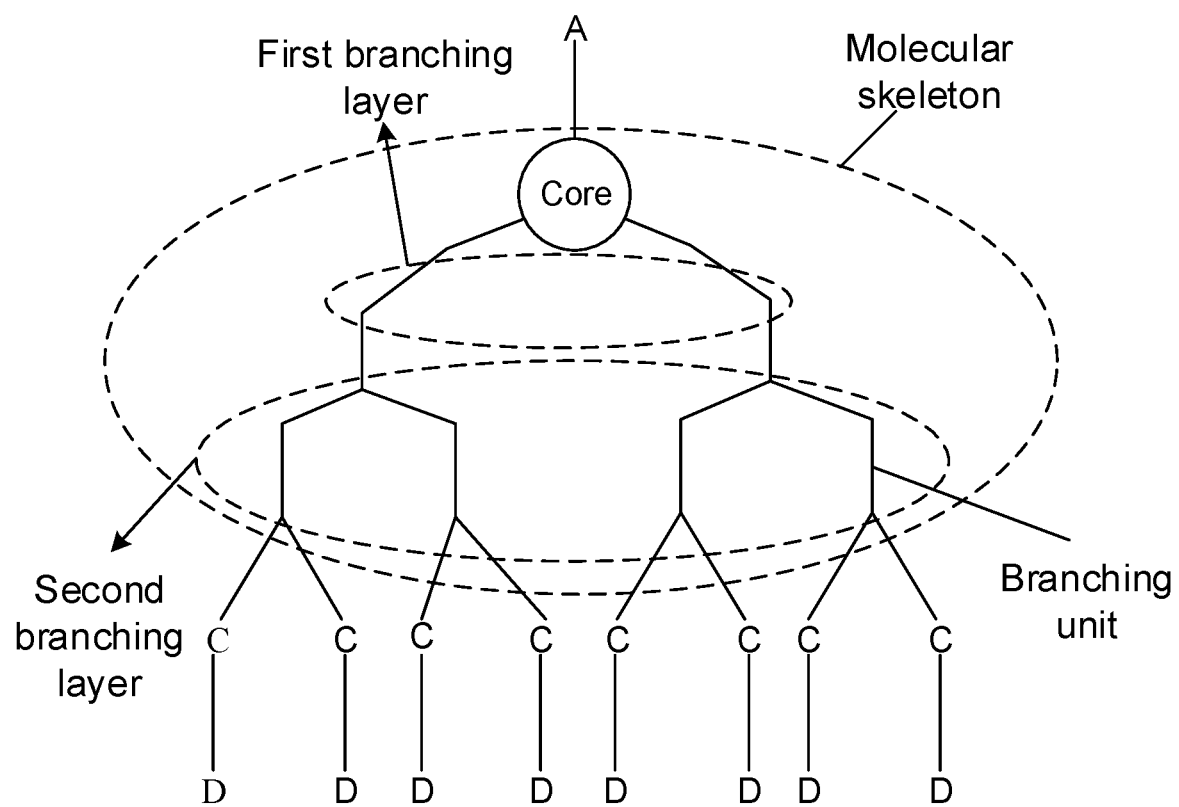
FIG. 13 is a structural diagram of yet another ligand, in accordance with some embodiments.

As shown in FIGS. 12 and 13, the dendritic molecular skeleton includes a core and a plurality of branching units, and a plurality of cavities are formed between the plurality of branching units. The core may be any one of a single atom (such as a nitrogen atom), a dendritic structure (such as a triphenylamine), a linear chain structure (such as an alkane or an olefin) or an annular structure (such as an aromatic hydrocarbon, a fluorene or a carbazole).

Each branching unit may be a linear chain bonding group or a dendritic bonding group. Herein, relative to the linear chain bonding group, the dendritic bonding group is a bonding group having a plurality of branches (that is, a structure in which branch chains are connected to a main chain). The linear chain bonding group or the dendritic bonding group may include at least one of an alkane bonding group, an olefin bonding group, or an aromatic hydrocarbon bonding group.

In some examples, the molecular skeleton in the ligand 100 is the dendritic molecular skeleton. Due to the strong force between the dendritic molecular skeleton and a solvent, the solubility of quantum dots in the solvent may be enhanced, which is conducive to the film formation of multi-coordinated quantum dots (i.e., quantum dots coordinated with a plurality of coordinating groups).

FIGS. 12 and 13 only show an example in which the branching unit is an alkane bonding group. A methine group (≡CH) may be formed at an end of the branching unit to branch, so as to be connected to a plurality of peripheral groups. For example, a peripheral group is a first coordinating group A or an initial group C.

For example, as shown in FIG. 12, the dendritic molecular skeleton may have a single branching layer, and the dendritic molecular skeleton is referred to as a first generation molecular skeleton. The first coordinating group A may be connected to the core, and the initial groups C (i.e., serving as the peripheral groups) may be connected to the branching layer.

For example, as shown in FIG. 13, on a basis of the already formed first generation molecular skeleton shown in FIG. 12, functional groups at an end of the first generation molecular skeleton may continue to react with a plurality of branching units having branching structures to form a molecular skeleton including a first branching layer (i.e., the branching layer in the first generation molecular skeleton) and a second branching layer. In this case, the molecular skeleton formed is referred to a second generation molecular skeleton. Similarly, functional groups at the end of each generation of the molecular skeleton may continue to react with a plurality of branching units having branching structures, so that a dendritic molecular skeleton with a higher generation may be obtained. For an N-th generation molecular skeleton (N being a positive integer), the first coordinating group A and the initial groups C may both be connected to any one of the branching layers (such as the first branching layer or the second branching layer shown in FIG. 13) or the core. FIG. 13 only shows an example in which the first coordinating group A is connected to the core and the initial groups C are connected to the second branching layer.

In some embodiments, as shown in FIGS. 11 to 13, the first coordinating group A and the at least one initial group C are both connected to the periphery of the molecular skeleton. In this way, a spatial distance between the first coordinating group A and the initial group C is large, after the initial group C is deprotected, it is conducive to the coordination of the formed second coordinating group B with the quantum dots around it.

That is, in a case where the molecular skeleton in the ligand 100 includes a linear chain molecular skeleton, as shown in FIG. 11, the first coordinating group A may be connected to one end of the linear chain molecular skeleton, and the initial group C may be connected to the other end of the linear chain molecular skeleton.

That is, in a case where the molecular skeleton in the ligand 100 includes a dendritic molecular skeleton, as shown in FIGS. 12 and 13, the first coordinating group A may be connected to the core of the dendritic molecular skeleton. The at least one initial group C includes a plurality of initial groups C, and each initial group C (i.e., serving as the peripheral group) is connected to an end of a corresponding one of the plurality of branching units of the dendritic molecular skeleton away from the core.

In some other embodiments, the first coordinating group A and the initial group C may also be both connected to ends of corresponding branching units of the plurality of branching units of the dendritic molecular skeleton away from the core.

In some embodiments, the molecular skeleton is a molecular skeleton capable of transporting carriers.

For example, the molecular skeleton capable of transporting carriers is configured as a molecular skeleton capable of transporting holes (also referred to as a hole transport molecular skeleton). In this case, the molecular skeleton has a strong capability of transporting holes. For example, the molecular skeleton capable of transporting holes includes one of a triphenylamine molecular skeleton, a carbazole molecular skeleton, or a fluorene molecular skeleton.

Or, the molecular skeleton capable of transporting carriers is configured as a molecular skeleton capable of transporting electrons (also referred to as an electron transport molecular skeleton). In this case, the molecular skeleton has a strong capability of transporting electrons. For example, the molecular skeleton capable of transporting electrons includes one of a pyridine molecular skeleton, a naphthalene molecular skeleton or a triazole molecular skeleton.

Based on this, different types of molecular skeletons may be selected according to light-emitting types of the quantum dots to be coordinated with the ligand 100.

For example, in a case where the quantum dots to be coordinated are blue light quantum dots, the molecular skeleton capable of transporting electrons may be selected as the molecular skeleton in the ligand 100, so as to improve the capability of transporting electrons to the quantum dots. Or, in a case where the quantum dots to be coordinated are red light quantum dots or green light quantum dots, the molecular skeleton capable of transporting holes may be selected as the molecular skeleton in the ligand 100, so as to improve the capability of transporting holes to the quantum dots.

In this way, in a case where the molecular skeleton in the ligand 100 provided by the embodiments is the molecular skeleton capable of transporting carriers, the luminescence performance of the quantum dots coordinated with the ligand 100 may be improved.

Figure 14:
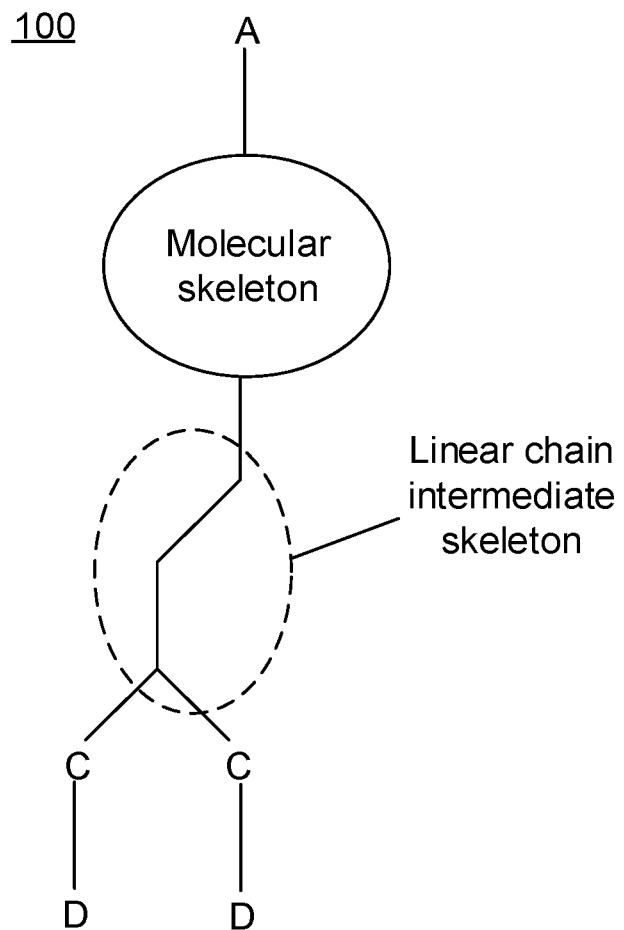
FIG. 14 is a structural diagram of yet another ligand, in accordance with some embodiments.
Figure 15:
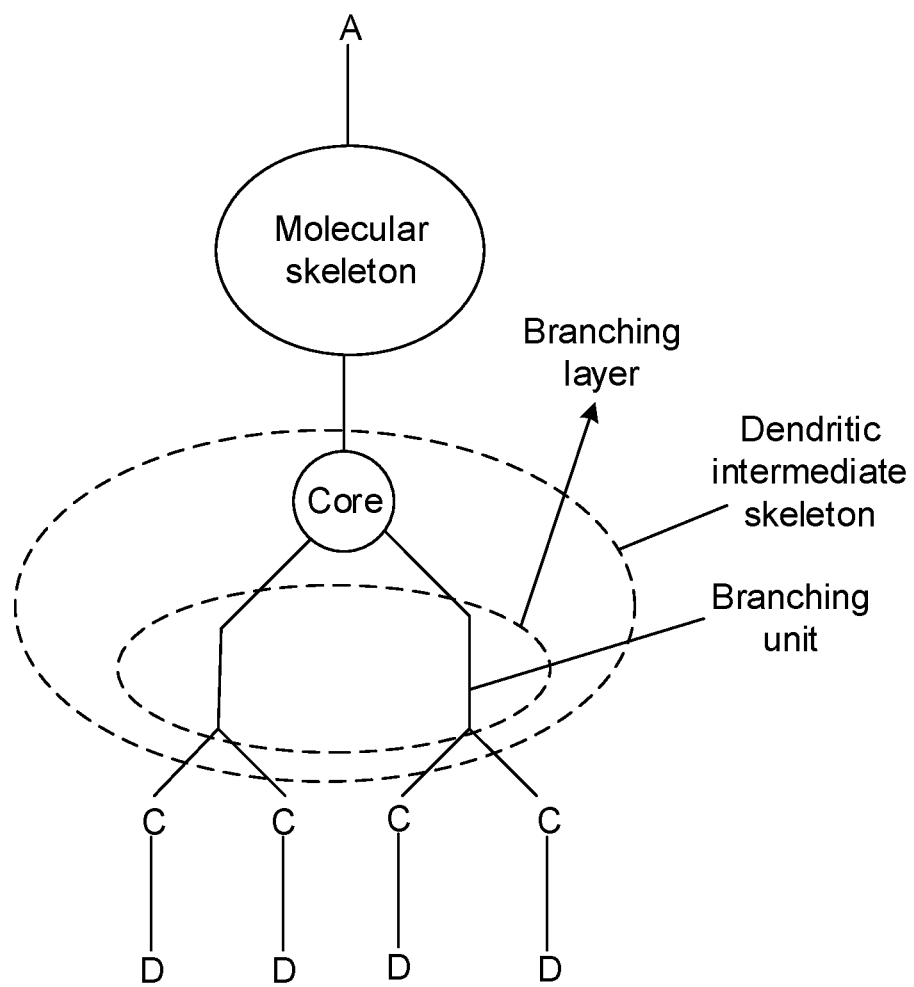
FIG. 15 is a structural diagram of yet another ligand, in accordance with some embodiments.
Figure 16:
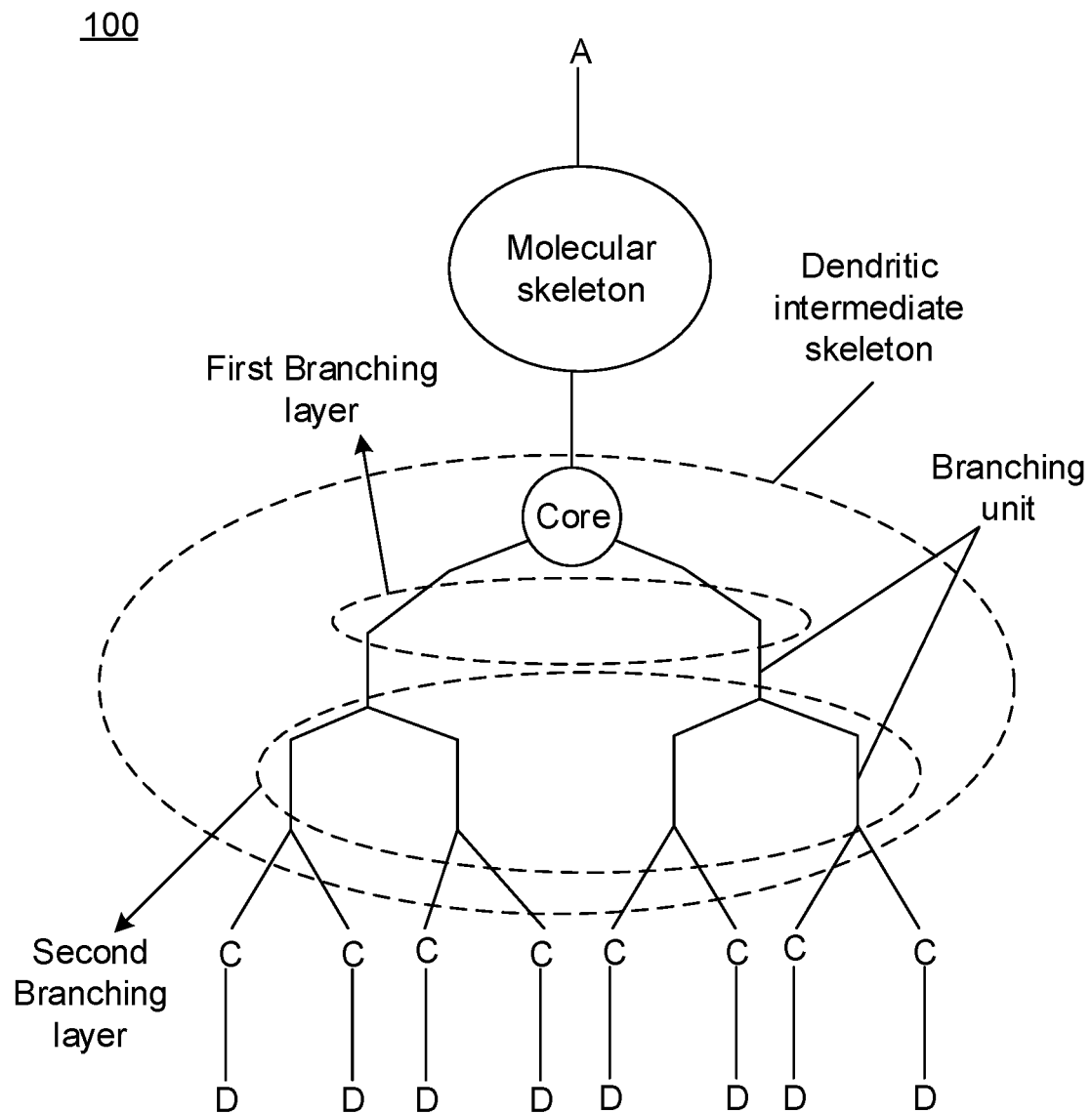
FIG. 16 is a structural diagram of yet another ligand, in accordance with some embodiments.

In some embodiments, as shown in FIGS. 14 to 16, the ligand 100 may further include an intermediate skeleton connected to the molecular skeleton. The intermediate skeleton may further expand the structure of the ligand 100, so that the ligand 100 may be provided with more coordinating groups therein, which is conducive to the coordination of the ligand 100 with more quantum dots. The at least one initial group C is connected to the molecular skeleton through the intermediate skeleton, or both the first coordinating group A and the at least one initial group C may be connected to the molecular skeleton through the intermediate skeleton. That is, the intermediate skeleton is connected the molecular skeleton to the at least one initial group C, or the intermediate skeleton is connected the molecular skeleton to both the first coordinating group A and the at least one initial group C.

Herein, FIGS. 14 to 16 only show an example in which the initial groups C are connected to the intermediate skeleton, and the first coordinating group A is directly connected to the molecular skeleton. However, the embodiments of the present disclosure are not limited thereto. It will be understood that both the first coordinating group A and the initial group C may be connected to the molecular skeleton through the intermediate skeleton.

In some embodiments, as shown in FIGS. 14 to 16, the intermediate skeleton may include a linear chain intermediate skeleton or a dendritic intermediate skeleton. The force between the dendritic intermediate skeleton and the solvent is strong, which may further improve the solubility of the quantum dots, and is conducive to the process of quantum dot film formation.

Relative to the linear chain intermediate skeleton, the dendritic intermediate skeleton may be an intermediate skeleton having a plurality of branches (that is, a structure in which branch chains are connected to a main chain). Similar to the above dendritic molecular skeleton, the dendritic intermediate skeleton refers to an intermediate skeleton having a dendritic structure. The dendritic intermediate skeleton may also be synthesized through repeated propagation reactions, and a branching layer is increased in each propagation reaction, referred to as a "generation".

The dendritic intermediate skeleton includes a core and a plurality of branching units, and a plurality of cavities are formed between the plurality of branching units. As shown in FIGS. 15 and 16, the core may be any one of a single atom (such as a nitrogen atom), a dendritic structure (such as a triphenylamine), a linear chain structure (such as an alkane, or an olefin) or an annular structure (such as an aromatic hydrocarbon, a fluorene or a carbazole). Each branching unit may be a linear chain bonding groups or a dendritic bonding group. Herein, relative to the linear chain bonding group, the dendritic bonding group may be a bonding group having a plurality of branches (that is, a structure in which branch chains are connected to a main chain).

The linear chain bonding group or the dendritic bonding group may include at least one of an alkane bonding group, an olefin bonding group, or an aromatic hydrocarbon bonding group. FIGS. 15 and 16 only show an example in which the plurality of branching units are alkane bonding groups. In this case, a methine group (≡CH) may be formed at an end of each branching unit to branch, so as to be coordinated with a plurality of peripheral groups. For example, a peripheral group is a first coordinating group A or an initial group C.

For example, as shown in FIG. 15, the dendritic intermediate skeleton may have only one branching layer, and the dendritic molecular skeleton refers to a first generation intermediate skeleton. The first coordinating group A and the initial group C may both be connected to the branching layer.

Or, as shown in FIG. 16, on the basis of the already formed first generation intermediate skeleton shown in FIG. 15, functional groups at an end of the first generation intermediate skeleton may continue to react with a plurality of branching units having branching structures to form an intermediate skeleton including a first branching layer (i.e., the branching layer in the first generation intermediate skeleton) and a second branching layer. In this case, the intermediate skeleton is referred to as a second generation intermediate skeleton. Similarly, functional groups at the end of each generation of the intermediate skeleton may continue to react with a plurality of branching units having branching structures, so that a dendritic intermediate skeleton with a higher generation may be obtained. For an N-th generation intermediate skeleton (N being a positive integer), the first coordinating group A and the at least one initial group C may both be connected to any one of the branching layers (such as the first branching layer or the second branching layer shown in FIG. 16). FIG. 16 only shows an example in which the first coordinating group A is connected to the molecular skeleton, and the initial groups C are connected to the second branching layer of the dendritic intermediate skeleton.

Some embodiments of the present disclosure provide a method of manufacturing the ligand 100, which includes the following steps.

A first compound containing the first coordinating group A reacts with a second compound containing the at least one initial group C and the protecting group D connected to each initial group C, so as to obtain the ligand 100.

Figure 17:
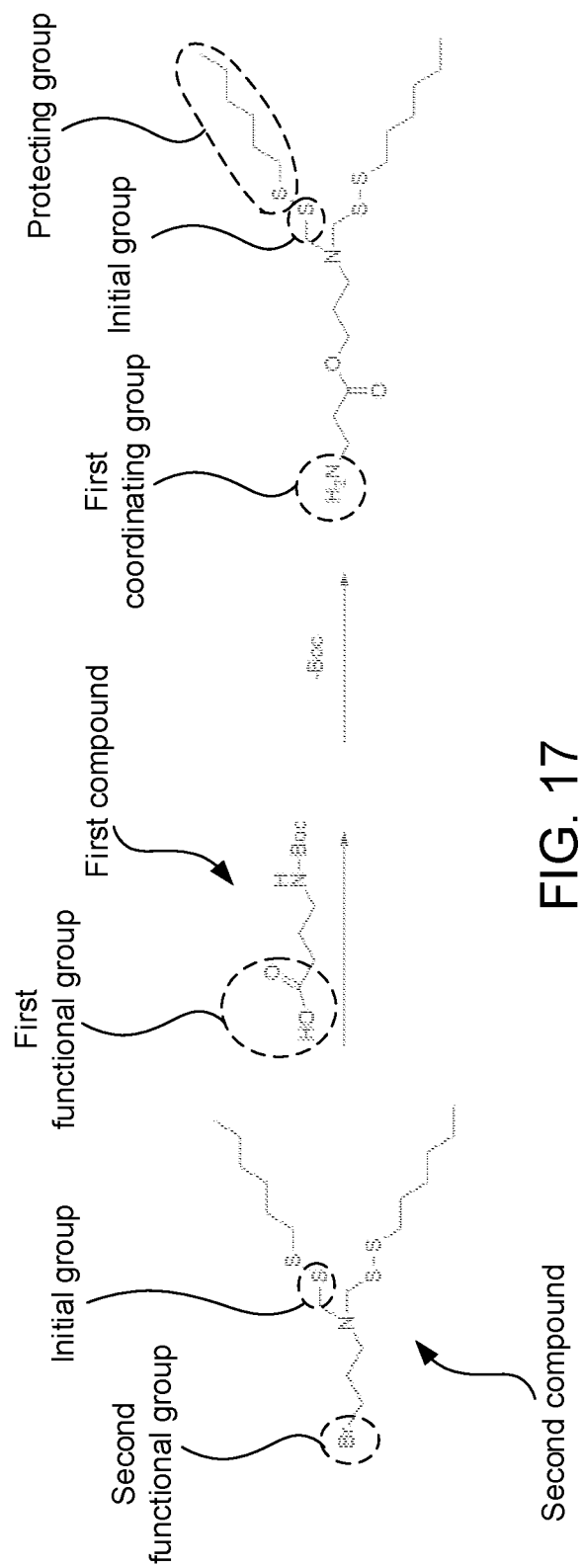
FIG. 17 is diagram showing a reaction equation of forming a ligand, in accordance with some embodiments.

A reaction equation of forming the ligand is shown in FIG. 17. As shown in FIG. 17, a first compound

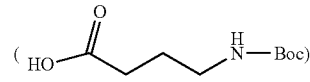

containing the first coordinating group A reacts with a second compound

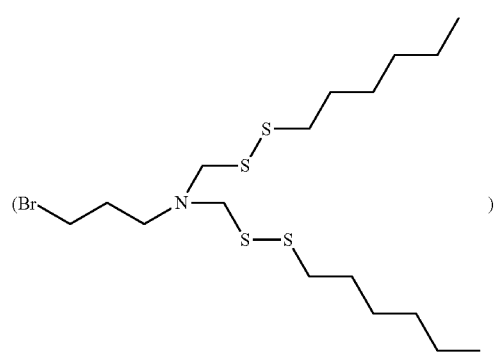

containing the at least one initial group C (i.e., "—S—" in FIG. 17), so as to obtain the ligand 100

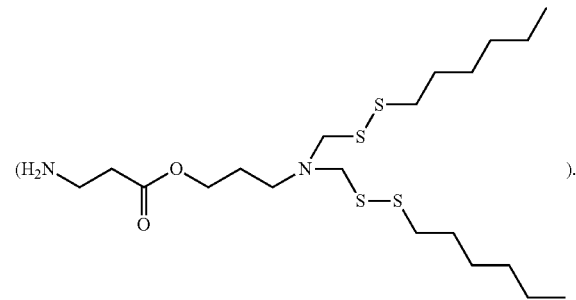

As shown in FIG. 17, the first compound containing the first coordinating group A may further contain a first functional group, and the second compound containing the at least one initial group C may further contain a second functional group. The first compound and the second compound may react through the first functional group and the second functional group, so as to obtain the ligand 100.

The first functional group and the second functional group are any functional groups that may react under suitable reaction conditions, so as to connect the first compound to the second compound. As shown in FIG. 17, the first functional group may be a carboxyl group (—COOH), and the second functional group may be a halogen (such as a bromine, —Br). In this case, the first functional group and the second functional group may perform a coupling reaction under a catalytic action.

Beneficial effects of the method of manufacturing the ligand 100 provided by the embodiments of the present disclosure are the same as beneficial effects of the ligand 100 provided by the embodiments of the present disclosure, and details are not described herein again.

Herein, there may be a plurality of methods to obtain the second compound containing the at least one initial group C and the protecting group D connected to each initial group C.

For example, in a first possible method, a reactant containing the at least one initial group C may directly react with another reactant containing the at least one protecting group D, so as to obtain the second compound.

Figure 18:
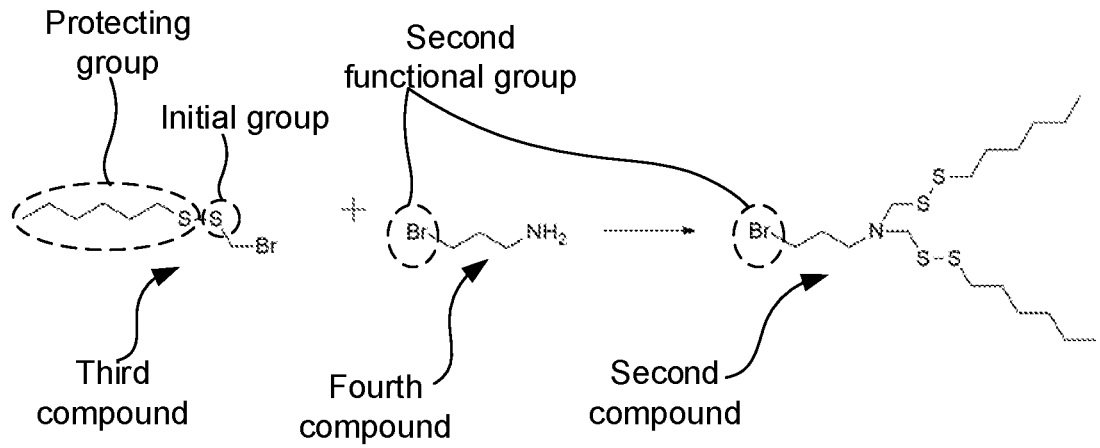
FIG. 18 is diagram showing a reaction equation of forming a second compound, in accordance with some embodiments.

Or, in a second possible method, a reaction equation of forming the second compound is shown in FIG. 18. As shown in FIG. 18, a third compound containing the at least one initial group C and each initial group C connected to a protecting group D reacts with a fourth compound, so as to obtain the second compound. The fourth compound may contain the second functional group (such as the bromine (—Br) shown in FIG. 18). The second functional group may reacts with a first functional group (such as the carboxyl group (—COOH) shown in FIG. 17) contained in the first compound containing the first coordinating group A, so as to form the ligand 100. As shown in FIG. 18, the third compound

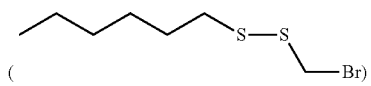

reacts with the fourth compound

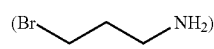

to form the second compound

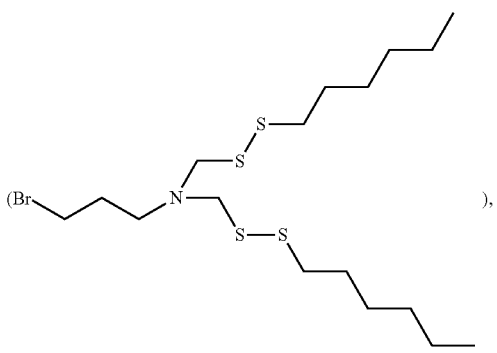

and the initial group C and the protecting group D in the third compound form a decomposable bond

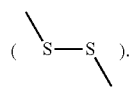

In some embodiments, the first coordinating group A in the first compound may also be in a state of being protected. For example, as shown in FIG. 17, the nitrogen atom of the first coordinating group A in the first compound is protected by a tert-butoxycarbonyl (—Boc). During the reaction of the first compound and the second compound to form the ligand 100, the tert-butoxycarbonyl is detached to expose the amino group (—NH$_2$). In this way, the obtained ligand 100 includes the first coordinating group A. Before the formation of the ligand 100, both the first coordinating group A and the initial groups C are in a state of being protected, which may prevent the coordinating groups from being damaged during the reaction.

Figure 19:
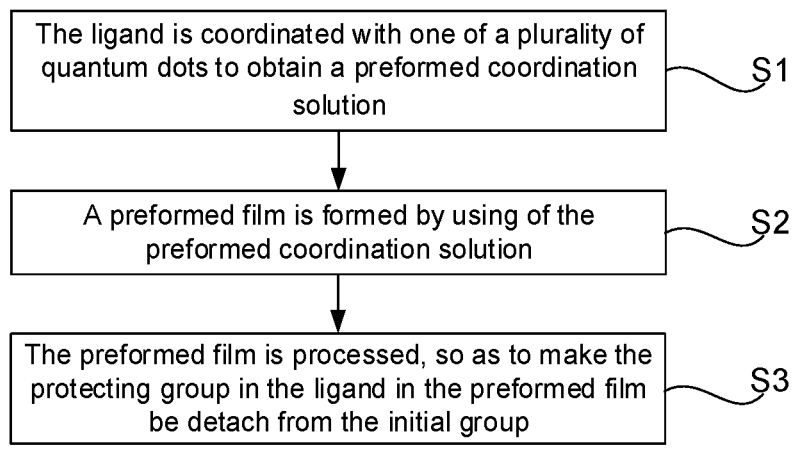
FIG. 19 is a flow chart of a method of manufacturing a quantum dot film, in accordance with some embodiments.

Some embodiments of the present disclosure provide a method of manufacturing the quantum dot film. FIG. 19 is a flow chart of a method of manufacturing the quantum dot film. As shown in FIG. 19, the method includes steps 1 (S1) to step 3 (S3).

In S1, the ligand 100 is coordinated with one of a plurality quantum dots to obtain a preformed coordination solution.

The preformed coordination solution contains a coordination compound formed through the ligand 100 and the quantum dot. The preformed coordination solution further includes a solvent used to dissolve and disperse the quantum dots in the process of forming the quantum dots.

There may be a plurality of possible methods to perform a coordination reaction between the ligand 100 and the quantum dot to obtain the preformed coordination solution.

For example, a first possible method includes: performing a coordination reaction between ligand 100 and the quantum dot directly, so as to obtain the preformed coordination solution.

Or, a second possible method includes: providing a quantum dot coordinated with a pre-ligand, and performing a ligand interchange reaction between the ligand 100 and the quantum dot coordinated with the pre-ligand, so as to obtain the preformed coordination solution.

The pre-ligand may include at least one of an oleic acid ligand, a stearic acid ligand, an oleylamine ligand or an octadecylamine ligand. For example, the pre-ligand is added into a precursor of the quantum dot in the process of forming the quantum dot, so as to adjust the growth rate, the crystal morphology, and the distribution of the size of the crystal of the quantum dot. For a same central atom on the surface of the quantum dot, a coordination capability of the pre-ligand to the central atom is weaker than a coordination capability of the first coordinating group A to the central atom. In this way, the ligand interchange reaction can be performed between the ligand 100 and the quantum dot coordinated with the pre-ligand.

In S2, a preformed film is formed by using of the preformed coordination solution.

For example, a surface of a substrate may be coated with the preformed coordination solution by a spin coating process, so as to form the preformed film. Herein, the substrate may be, for example, a substrate provided with a TFT array and the anode of the quantum dot light-emitting device thereon.

In S3, the preformed film is processed, so as to make the protecting group D in the ligand 100 in the preformed film be detach from the initial group C.

In the embodiments of the present disclosure, in the preformed coordination solution, the initial group C in the ligand 100 is connected to the protecting group D, so that the first coordinating group A is coordinated with the quantum dot only. In this way, the solubility of the quantum dots in the preformed coordination solution may be improved. After the preformed film is formed, the protecting group D is detached from the initial group C, and the second coordinating group B is formed after the initial group C is deprotected. The second coordinating group B may be coordinated with another quantum dot around it. Therefore, a network molecular structure may be formed, so that the ligand 100 and the quantum dots are more stably combined to each other.

In the ligand 100, the decomposable bond is formed between the protecting group D and the initial group C, and the decomposable bond may be selected as a chemical bond that decomposes under UV light irradiation or by heating to avoid deprotection under coordination conditions.

In some embodiments, the step of processing the preformed film, so as to make the protecting group D in the ligand in the preformed film be detached from the initial group C, includes: irradiating the preformed film by using of UV light or heating the preformed film, so as to make the protecting group D in the ligand 100 in the preformed film be detached from the initial group C.

Herein, different processing methods may be selected to process the preformed film according to the different decomposable bonds formed between the protecting group D and the initial group C in the ligand 100. For example, in a case where the decomposable bond formed between the protecting group D and the initial group C in the ligand 100 includes an azo bond, a peroxy bond, an acetophenone bond, a disulfide bond, an episulfide bond or other photolytic chemical bonds, UV light may be used to irradiate the preformed film to make the protecting group D be detached from the initial group C. Or, in a case where the decomposable bond formed between the protecting group D and the initial group C in the ligand 100 includes an amide bond, an ester bond, an ether bond or other pyrolytic chemical bonds, the preformed film may be heated to make the protecting group D be detached from the initial group C.

In some embodiments, the method of manufacturing the quantum dot film further includes: adding methanol to the preformed film to dissolve at least one of the detached protecting group D or sub-groups decomposed from the detached protecting group D; and removing the methanol.

For example, the methanol may be dropwise added on a surface of the preformed film, or the preformed film may be wiped or coated with a water absorbent material impregnated with the methanol to remove at least one of the detached protecting group D or sub-groups decomposed from the detached protecting group D.

For example, a reaction equation shown in FIG. 18 is taken as an example. After the preformed film is formed, the protecting group D

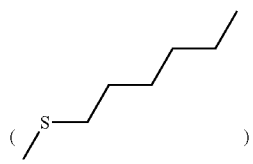

is detached from the initial group C (—S—) by UV irradiation. During the irradiation, the protecting group D may be decomposed into a plurality of sub-groups (i.e., a plurality of small molecular fragments). In this case, in a case where the ligand 100 includes a plurality of protecting group D, the methanol is dropwise added on the preformed film to dissolve some detached protecting groups D and the decomposed sub-groups, and then the methanol is removed by rotary evaporation, so as to remove the detached protecting groups D and the decomposed sub-groups.

In some embodiments, the method of manufacturing the quantum dot film further includes: performing a heat treatment on the preformed film. For example, the preformed film is heated at approximately 120° C. for approximately 20 minutes to remove the solvent of the quantum dots.

The foregoing descriptions are merely specific implementation manners of the present disclosure, but the protection scope of the present disclosure is not limited thereto. Any person skilled in the art could conceive of changes or replacements within the technical scope of the present disclosure, which shall all be included in the protection scope of the present disclosure. Therefore, the protection scope of the present disclosure shall be subject to the protection scope of the claims.

What is claimed is:

1. A ligand, comprising:
    a molecular skeleton;
    a first coordinating group connected to the molecular skeleton;
    at least one initial group connected to the molecular skeleton; and
    a protecting group connected to an end of each initial group away from the molecular skeleton,
    wherein each initial group is capable of forming a second coordinating group after deprotection, and
    wherein a chemical structural formula of the ligand is:

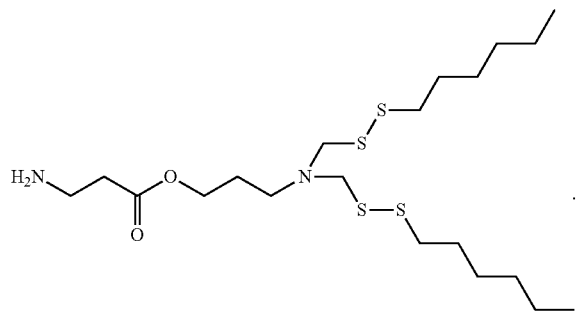 [SMILES: CCCCCCSSCN(CCCOC(=O)CCN)CSSCCCCCC]

2. A method of manufacturing the ligand according to claim 1, comprising:
    performing a reaction between a first compound containing the first coordinating group and a second compound containing the at least one initial group and the protecting group connected to each initial group, to obtain the ligand,
    wherein a chemical structural formula of the first compound is:

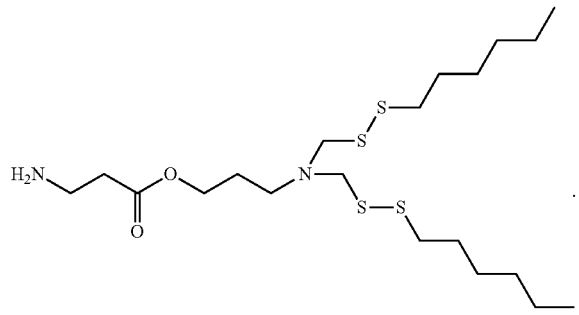 [SMILES: CCCCCCSSCN(CCCOC(=O)CCN)CSSCCCCCC]

and a chemical structural formula of the second compound is:

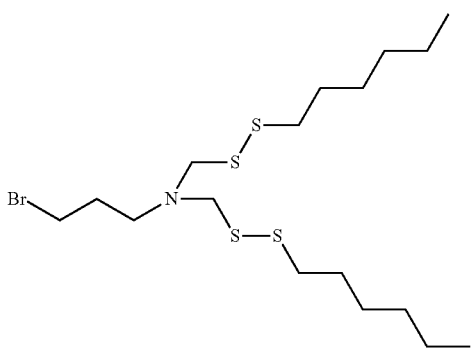

3. A quantum dot film, comprising:
a plurality of quantum dots; and
a ligand coordinated with at least one of the plurality of quantum dots; wherein the ligand is the ligand according to claim 1, including at least one second coordinating group correspondingly formed after the at least one initial group is deprotected.

4. A display apparatus, comprising:
a base substrate; and
a quantum dot light-emitting device disposed on the base substrate; wherein the quantum dot light-emitting device includes the quantum dot film according to claim 3.

5. A method of manufacturing a quantum dot film, comprising:
performing a coordination reaction between the ligand according to claim 1 and a quantum dot of a plurality quantum dots, to obtain a preformed coordination solution;
forming a preformed film by using of the preformed coordination solution; and
processing the preformed film, so as to make the protecting group in the ligand in the preformed film be detached from each initial group to form the second coordinating group;
wherein the second coordinating group is coordinated with the quantum dot or another of the plurality quantum dots.

6. The method according to claim 5, wherein performing the coordination reaction between the ligand and the quantum dot, to obtain the preformed coordination solution, includes:
performing a coordination reaction between the ligand and the quantum dot directly, so as to obtain the preformed coordination solution; or,
providing a quantum dot coordinated with a pre-ligand; and
performing a ligand interchange reaction between the ligand and the quantum dot coordinated with the pre-ligand, so as to obtain the preformed coordination solution; wherein for a same central atom on a surface of the quantum dot coordinated with the pre-ligand, a coordination capability of the pre-ligand to the central atom is weaker than a coordination capability of the first coordinating group to the central atom.

7. The method according to claim 5, wherein processing the preformed film, so as to make the protecting group in the ligand in the preformed film be detached from each initial group, includes:
irradiating the preformed film by using of UV light or heating the preformed film, so as to make the protecting group in the ligand in the preformed film be detached from each initial group.

8. The method according to claim 7, wherein after the preformed film is processed, the method further comprises:
adding methanol to the preformed film to dissolve at least one of the detached protecting group or sub-groups decomposed from the detached protecting group; and
removing the methanol.

* * * * *

UNITED STATES PATENT AND TRADEMARK OFFICE
CERTIFICATE OF CORRECTION

PATENT NO. : 11,530,350 B2
APPLICATION NO. : 17/032546
DATED : December 20, 2022
INVENTOR(S) : Wenhai Mei Page 1 of 1

It is certified that error appears in the above-identified patent and that said Letters Patent is hereby corrected as shown below:

In the Claims

In Claim 2, Line 51-65, the chemical structure formula should read as follows:

Signed and Sealed this
Ninth Day of May, 2023

Katherine Kelly Vidal
*Director of the United States Patent and Trademark Office*